United States Patent

Aida et al.

Patent Number: 5,744,678
Date of Patent: Apr. 28, 1998

[54] OLIGOMERIZATION CATALYSTS AND PROCESS USING THE SAME FOR THE PRODUCTION OF OLEFINIC OLIGOMERS

[75] Inventors: Fuyuki Aida; Takashi Nakano; Yoshio Tajima; Kazuo Matsuura, all of Yokohama, Japan

[73] Assignee: Nippon Oil Co., Ltd., Tokyo, Japan

[21] Appl. No.: 737,077

[22] PCT Filed: Mar. 6, 1996

[86] PCT No.: PCT/JP96/00532

§ 371 Date: Nov. 1, 1996

§ 102(e) Date: Nov. 1, 1996

[87] PCT Pub. No.: WO96/27440

PCT Pub. Date: Sep. 12, 1996

[30] Foreign Application Priority Data

| Mar. 6, 1995 | [JP] | Japan | 7-083049 |
| Apr. 5, 1995 | [JP] | Japan | 7-115344 |
| Jul. 20, 1995 | [JP] | Japan | 7-206607 |
| Jul. 20, 1995 | [JP] | Japan | 7-206608 |
| Sep. 5, 1995 | [JP] | Japan | 7-251760 |
| Sep. 5, 1995 | [JP] | Japan | 7-251761 |
| Sep. 8, 1995 | [JP] | Japan | 7-230984 |
| Sep. 8, 1995 | [JP] | Japan | 7-230985 |

[51] Int. Cl.$^6$ .................. C07C 2/18; C07C 2/22

[52] U.S. Cl. .......... 585/513; 585/521; 585/522; 585/523; 585/524; 585/525; 585/527; 585/531; 502/113; 502/114; 502/115; 502/116; 502/117; 502/121; 502/125; 502/126; 502/128; 502/129; 502/131; 502/133; 502/134

[58] Field of Search .................. 585/513, 523, 585/524, 525, 527, 531, 521, 522; 502/113, 114, 115, 116, 117, 121, 125, 126, 128, 129

[56] References Cited

U.S. PATENT DOCUMENTS

| 3,513,218 | 5/1970 | Faltings et al. |
| 3,755,490 | 8/1973 | Yoo et al. |
| 4,155,946 | 5/1979 | Sato et al. ............ 585/513 |
| 4,992,610 | 2/1991 | Sato et al. ............ 585/513 X |
| 5,245,097 | 9/1993 | Wu ............ 585/513 |
| 5,260,499 | 11/1993 | Wu ............ 585/512 |
| 5,286,695 | 2/1994 | Hirose et al. ............ 585/513 X |
| 5,349,115 | 9/1994 | Nomura et al. ............ 585/513 |

OTHER PUBLICATIONS

Hackh's Chem. Dictionary (4th ed.) McGraw-Hill, N.Y., N.Y., 646 (1969).

*Primary Examiner*—Fred Teskin
*Attorney, Agent, or Firm*—Panitch Schwarze Jacobs & Nadel, P.C.

[57] ABSTRACT

An oligomerization catalyst according to the invention comprises a nickel compound (A); an organophosphoric compound (B); an organoaluminum compound (C); and a compound of the group consisting of carbon-halogen bond-containing compounds, oxoacid and salts thereof, sulfonic acid and derivatives thereof, and compounds of any of the formulae $QX^4{}_n$, $QR_n$, $QR'_n$, $QX^4{}_1R_m$, $QX^4{}_1R'_m$, $QR_1R'_m$, $Q^1(BR_4)_p$ and $R''(BR_4)$ wherein Q is an element of the group consisting of Mg, Ti, Zr, B and Sn, $Q^1$ is an element of the group consisting of Li, Na, K, Ca and Zn, $X^4$ is a halogen or hydrogen atom, R is a $C_1$–$C_{12}$ hydrocarbon group, R' is a $C_1$–$C_{12}$ oxygen-containing hydrocarbon group, R'' is a $C_1$–$C_{20}$ hydrocarbon group or an ammonium group, n is a valence of Q, l, m is a natural member that satisfied n=l+m, and p is a valence of $Q^1$. This catalyst is useful for the production of alpha-olefinic oligomers.

18 Claims, No Drawings

OLIGOMERIZATION CATALYSTS AND PROCESS USING THE SAME FOR THE PRODUCTION OF OLEFINIC OLIGOMERS

CROSS-REFERENCE TO RELATED APPLICATION

This application is a 35 U.S.C. §371 filing of International Application No. PCT/JA96/00532, filed 6 Mar. 1996.

FIELD OF THE INVENTION

This invention relates to catalysts useful for oligomerization of α-olefins and a process using the same for the production of α-olefinic oligomers.

BACKGROUND OF THE ART

Transition metal compounds have been widely used as the catalysts for oligomerization of olefins.

Japanese Patent Publication No. 47-49561 discloses the use of catalysts comprising nickel compounds, phosphine compounds and halogen-containing organoaluminum compounds for dimerization of lower olefins. The disclosed process is imposed with a restriction that the catalysts have to be prepared in the presence of lower olefins (gaseous) to be dimerized and further has a drawback in that the catalysts are not adequately stable or sometimes deficient in their activity, leading to reduced dimer yields (catalytic activity) for a given amount of catalyst.

Japanese Patent Publication No. 62-19408 discloses catalysts comprising nickel compounds, bis-dialuminoxanes and halogenated phenols for use in dimerizing α-olefins. The catalysts disclosed therein are superior to those disclosed in Patent Publication No. 47-49561 in respect of catalytic activity and stability, but have the difficulty that when used for a propylene feedstock, they are prone to by-produce large quantities of trimers with a dimer selectivity reduced to the order of 50%–70%.

Whereas, it is an object of the present invention to provide a novel oligomerization catalyst capable of selectively producing α-olefinic dimers at an increased rate of yield.

It is another object of the invention to provide a process using the above inventive catalyst for the production of α-olefinic oligomers.

DESCRIPTION OF THE INVENTION

An oligomerization catalyst according to the invention comprises the following components (A) through (D):

component (A) which is one or more of nickel compounds of the group consisting of a nickel salt of an organic acid, a nickel salt of an inorganic acid and a nickel complex;

component (B) which is one or more of organophosphoric compounds of the formula $$PX^1X^2X^3 \quad \ldots (I)$$

wherein $X^1$, $X^2$ and $X^3$ each are a halogen atom, a hydrogen atom or a $C_1$–$C_{12}$ hydrocarbon residual group;

component (C) which is one or more of organoaluminum compounds; and component (D) which is one or more of compounds of the group consisting of (a) carbon-halogen bond-containing compounds,
(b) oxoacid and salts thereof,
(c) sulfonic acid and derivatives thereof, and
(d) compounds of any of the formulae $$QX^4_n \quad \ldots (II)$$

$$QR_n \quad \ldots (III)$$

$$QR'_n \quad \ldots (IV)$$

$$QX^4_l R_m \quad \ldots (V)$$

$$QX^4_l R'_m \quad \ldots (VI)$$

$$QR_l R'_m \quad \ldots (VII)$$

$$Q^1(BR_4)_p \quad \ldots (VIII)$$

and $$R''(BR_4) \quad \ldots (IX)$$

wherein Q is an element of the group consisting of Mg, Ti, Zr, B and Sn, $Q^1$ is an element of the group consisting of Li, Na, K, Ca and Zn, $X^4$ is a halogen or hydrogen atom, R is a $C_1$–$C_{12}$ hydrocarbon group, R' is a $C_1$–$C_{12}$ oxygen-containing hydrocarbon group, R" is a $C_1$–$C_{20}$ hydrocarbon group or an ammonium group, n is a valence of Q, l, m is a natural number that satisfies n=l+m, and p is a valence of $Q^1$.

The process of the invention for the production of α-olefinic oligomers is carried into practice in the presence of the above defined catalyst.

The term nickel salt of an organic acid as used herein includes saturated aliphatic nickel carboxylates such as nickel formate, nickel acetate, nickel propionate, nickel octoate, nickel stearate and nickel 2-ethylhexanoate, and nickel naphthenates.

The term nickel salt of an inorganic acid designates nickel halides such as nickel chloride, nickel bromide, nickel fluoride and nickel iodide, nickel sulfate and nickel nitrate. There may be also used nickel hydroxide and nickel oxide as component (A).

The term nickel complex includes bis-(1,5-cyclooctadiene)-nickel, dichlorobis(triphenylphosphine)nickel, bis-cyclopentadienyl nickel, bis(acetylacetonate)nickel, bis(ethylacetoacetate)nickel and nickel carbonyl. Preferred are bis-(1,5-cyclooctadiene)-nickel, nickel acetate, nickel naphthenate, 2-ethylhexanate nickel, and bis(acetylacetonate)nickel. More preferred are nickel naphthenate, 2-ethylhexanate nickel, bis(acetylacetonate)nickel and bis(1,5-cyclooctadiene)nickel.

Component (B) according to the invention is a compound of the formula $$PX^1X^2X^3 \quad \ldots (I)$$

wherein at least two of $X^1$, $X^2$ and $X^3$ are $C_1$–$C_{12}$, preferably $C_1$–$C_8$ hydrocarbon moieties and the remaining one is a halogen or hydrogen atom.

At least two of $X^1$, $X^2$ and $X^3$ are a hydrocarbon group such as alkyl, aryl and aralkyl, or an oxygen-containing hydrocarbon group such as alkoxy and aryloxy, preferably including methyl, methoxy, ethyl, ethoxy, propyl, propoxy, isopropyl, isopropoxy, butyl, isobutyl, pentyl, cyclopentyl, hexyl, cyclohexyl, phenyl, phenoxy, tolyl, xylyl and benzyl. If either of $X^1$, $X^2$ and $X^3$ is halogen, this may be chlorine, bromine or fluorine, but chlorine is preferred.

Preferred examples of organophosphoric compounds (B) are trimethylphosphine, triethylphosphine, tripropylphosphine, triisopropylphosphine, tributylphosphine, triisobutylphosphine, tripentylphosphine, tricyclopentylphosphine, trihexylphosphine, tricyclohexylphosphine, triphenylphosphine, tritolylphosphine, diphenylphosphine, diphenylpropylphosphine, diphenylmethylphosphine, diphenylchlorophosphine, trimethylphosphite, triethylphosphite, tripropylphosphite, tributylphosphite, tripentylphosphite, tricyclopentylphosphite, trihexylphosphite, tricyclohexylphosphite, triphenylphosphite, tritolylphosphite, of which phosphine compounds are particularly preferred.

The type of organophosphoric compound chosen will largely affect the selectivity of dimers to be produced according to the invention. Triphenylphosphine is effective when selectively producing dimers having head-head or tail-tail bonds. If dimers having tail-tail bonds are desired, there may be preferably used triisopropylphosphine or tricyclohexylphosphine.

Component (C) according to the invention is represented in one group by the formula

$$AlR^1_pX_{3-p} \quad \ldots (XXIV)$$

wherein $R^1$ is a $C_1$–$C_{20}$, preferably $C_1$–$C_{12}$ hydrocarbon group, X is a hydrogen or halogen atom, and p is an integer that satisfies the range of $0 \leq n \leq 3$.

The designation p in the above formula XXIV need not necessarily be an integer, but can be for instance p=1.5 indicating $AlR^1_{1.5}X_{1.5}$; i.e. $R^1_3Al_2X_3$ which is an aluminum sesqui compound.

Hydrocarbon groups $R^1$ in formula (XXIV) include alkyl group, aryl group, aralkyl group, alkylaralkyl group, methyl group, ethyl group, propyl group, isopropyl group, butyl group, isobutyl group, pentyl group, cyclopentyl group, hexyl group, cyclohexyl group, phenyl group, tolyl group, xylyl group and benzyl group. If X is halogen, it may be fluorine, chlorine, bromine or iodine.

Specific examples of the above organoaluminum compound include trimethylaluminum, triethylaluminum, tripropylaluminum, tributylaluminum, triisobutylaluminum, tripentylaluminum, tricyclopentylaluminum, trihexylaluminum, tricyclohexylaluminum, triphenylaluminum, tritolylaluminum, dimethylaluminumchloride, diethylaluminumchloride, diisobutylaluminumchloride, ethylaluminumdichloride, isobutylaluminumdichloride, ethylaluminumsesquichloride, diethylaluminumhydride, diisobutylaluminumhydride, aluminumchloride, diethylaluminumchloride, ethylaluminumsesquichloride, among which diethylaluminumchloride and ethylaluminumsesquichloride are preferred.

The second group of organoaluminum compounds eligible for use in the invention embraces a modified organoaluminum compound resulting from reacting the formula (XXIV) compound with an active proton compound such as water, alcohol, phenol and the like, and may be represented by the formula $$AlR^2_q(OR^3)_{3-q} \quad \ldots (XXV)$$

wherein $R^2$ and $R^3$ each are a $C_1$–$C_{20}$, preferably a $C_1$–$C_{12}$ hydrocarbon group, and q is $0 < q \leq 3$.

$R^2$ and $R^3$ in the above formula each may be an alkyl, aryl, aralkyl or alkylaryl group, specifically including methyl, ethyl, propyl, isopropyl, butyl, isobutyl, pentyl, cyclopentyl, hexyl, cyclohexyl, phenyl, tolyl, xylyl and benzyl groups.

Modified organoaluminum compounds eligible for use as component (C) according to the invention include dimethylmethoxyaluminum, dimethylethoxyaluminum, dimethylphenoxyaluminum, dimethyl-(2,6-di-t-butyl-4-methylphenoxy)-aluminum, methyldimethoxyaluminum, methyldiethoxyaluminum, methyldiphenoxyaluminum, methyl-di(2,6-di-t-butyl-4-methylphenoxy)-aluminum, diethylmethoxyaluminum, diethylethoxyaluminum, diethylphenoxyaluminum, diethyl-(2,6-di-t-butyl-4-methylphenoxy)-aluminum, ethyldiphenoxyaluminum, ethyldimethoxyaluminum, ethyldiethoxyaluminum, ethyl-di (2,6-di-t-butyl-4-methylphenoxy)-aluminum and the like.

The above recited organoaluminum and modified organoaluminum compounds may be used in combination.

Component (D) used in the invention is identified as follows:

(1) Carbon-halogen bond-containing compound (Da)

This compound may be represented by the formulae

$$R^4\text{—}R^5_r \quad \ldots (XXVI)$$

$$R^4(A\text{—}R^5)_r \quad \ldots (XXVII)$$

wherein $R^4$ is a $C_1$–$C_{30}$ hydrocarbon group having part or whole of hydrogen substituted with halogen, $R^5$ is hydrogen, halogen or a $C_1$–$C_{30}$ hydrocarbon residual group, A is —O—, —OSiR$^6$—, —C(OR$^7$)— or —C(OR$^7$)$_2$O— (here, $R^6$ is hydrogen, halogen or a $C_1$–$C_{30}$ hydrocarbon residual groups, and $R^7$ is a $C_1$–$C_{30}$ hydrocarbon residual group), and r is $1 \leq r \leq 4$, preferably $1 \leq r \leq 3$, $R^5$, $R^6$ and $R^7$ may be the same or different, and $R^4$ and $R^5$ may be bonded together to form a ring.)

$R^4$ in the above formulae is a halogenated hydrocarbon group having part or whole of hydrogen in a $C_1$–$C_{30}$, preferably a $C_1$–$C_{20}$, more preferably a $C_1$–$C_{12}$ hydrocarbon group substituted with one or more of halogens including fluorine, chlorine, bromine and iodine, of which fluorine is particularly preferred. A precursor hydrocarbon group is a monovalent hydrocarbon group having one free valence or a polyvalent hydrocarbon group having 2–4 free valences. The monovalent hydrocarbon group typically includes alkyl groups such as of methyl, ethyl, propyl, isopropyl, cyclopropyl, butyl, isobutyl, tert-butyl, cyclopentyl, hexyl, isohexyl, cyclohexyl, heptyl, octyl, decyl and dodecyl; alkenyl groups such as vinyl and allyl; aryl groups such as phenyl, tolyl, xylyl, mesityl, indenyl and naphthyl group; aralkyl groups such as benzyl, trityl, phenethyl, styryl, benzhydryl, phenylbutyl, phenylpropyl, neophyl and the like. The divalent hydrocarbon group exemplarily includes alkylene groups such as of methylene, ethylene, propylene and butylene; arylene groups; and aryl alkylene groups. The tervalent hydrocarbon group exemplarily includes alkanetriyl group, arenetriyl group, arylalkanetriyl group. The tetravalent hydrocarbon group exemplarily includes arenetetrayl group, arylalkanetetrayl group and the like.

Noncyclic hydrocarbon chains in each of the above hydrocarbon groups may be straight or branched.

If either of the substituting groups $R^5$ and $R^6$ is halogen, this halogen should be either fluorine, chlorine, bromine or iodine.

The hydrocarbon residual groups $R^5$, $R^6$ and $R^7$ referred to above include hydrocarbon groups formed by carbons and hydrogen alone as well as those which have one or more of hydrogen atoms substituted with groups —OR$^8$ ($R^8$ is a $C_1$–$C_{20}$ hydrocarbon or halogenated hydrocarbon group) or with halogen (fluorine, chlorine, bromine and iodine). The hydrocarbon groups ($C_1$–$C_{30}$, preferably $C_1$–$C_{20}$, more preferably $C_1$–$C_{12}$) exemplarily include alkyl groups such as methyl group, ethyl group, propyl group, isopropyl group, cyclopropyl group, butyl group, isobutyl group, tert-butyl group, cyclopentyl group, hexyl group, isohexyl group, cyclohexyl group, heptyl group, octyl group, decyl group and dodecyl group; alkenyl groups such as vinyl group, allyl group; aryl group such as phenyl group, tolyl group, xylyl group, mesityl group, indenyl group and naphthyl group;

aralkyl group such as benzyl group, trityl group, phenethyl group, styryl group, benzhydryl group, phenylbutyl group, phenylpropyl group and neophyl group; alkylene group such as methylene group, ethylene group, propylene group, isopropylene group, cyclopropylene group, butylene group, isobutylene group, tert-butylene group, cyclobutylene group, pentylene group, isopentylene group, neopentylene group, cyclopentylene group, hexylene group, isohexylene group, cyclohexylene group, heptylene group and octyl group; arylene group such as phenylene group, mesitylene group, tolylene group, xylylene group, indenylene group, naphthylene group; aralkylene group such as benzylene group, tritylene group, phenethylene group, styrylene group and the like.

The compounds Da may be represented by the formulae

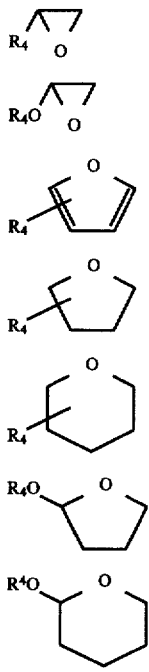

(X)
(XI)
(XII)
(XIII)
(XIV)
(XV)
(XVI)

$R^4-O-R^8$ (XVII)

$R^4-O-SiR^8{}_3$ (XVIII)

$R^4R^9C(OR^8)_2$ (XIX)

$R^8R^9C(OR^4)(OR^8)$ (XX)

$R^4C(OR^8)_3$ (XXI)

$R^8C(OR^4)(OR^8)_2$ (XXII)

and $R^4-R^{10}$ (XXIII)

$R^4$ in each of the above formulae is a $C_1$–$C_{30}$, preferably a $C_1$–$C_{20}$, more preferably a $C_1$–$C_{12}$ hydrocarbon group specifically including those of fluoromethyl, fluoroethyl, fluoropropyl, fluoroisopropyl, fluorocyclopropyl, fluorobutyl, fluoroisobutyl fluorotert-butyl, fluoropentyl, fluoroisopentyl, fluoroneopentyl, fluorocyclopentyl, fluorohexyl, fluoroisohexyl, fluorocyclohexyl, fluoroheptyl, fluorooctyl, fluorophenyl, fluorobenzyl, fluoromesityl, fluoroindenyl, fluoronaphthyl, trifluoroethyl, hexafluoroisopropyl, pentafluoropropyl, perfluorobutylethyl, perfluoroethyl, perfluorodecylethyl, perfluoroethylhexyl, perfluorobutylhexyl, perfluorohexylhexyl, perfluorooctylhexyl, perfluoroisoamylethyl, perfluoroisononylethyl, perfluoroisopropylhexyl, perfluoroisoamylhexyl, perfluoroisononylhexyl, tetrafluoropropyl, octafluoropentyl, dodecafluoroheptyl, hexadecafluorononyl, bis (trifluoromethyl)propyl, hexafluorobutyl, perfluorohexyliodopropyl, perfluorooctyliodopropyl, perfluoroisoheptyliodopropyl, perfluoroisononyliodopropyl, octafluoropropyl, perfluorobutyl, octafluorocyclobutyl, perfluoropentyl, perfluorocyclopentyl, perfluorohexyl, perfluorocyclohexyl, perfluoroheptyl, perfluorocycloheptyl, perfluorooctyl, perfluorocyclooctyl, perfluorononyl, perfluorocyclononyl, perfluorodecyl, perfluorocyclodecyl, perfluoroundecyl, perfluorocycloundecyl, perfluorododecyl, perfluorocyclododecyl, perfluorotridecyl, perfluorocyclotridecyl, perfluorotetradecyl, perfluorocyclotetradecyl, perfluoropentadecyl, perfluorocyclopentadecyl, perfluorohexadecyl, perfluorocyclohexadecyl, perfluoroheptadecyl, perfluorocycloheptadecyl, perfluorooctadecyl, perfluorocyclooctadecyl, perfluorononadecyl, perfluorocyclononadecyl, perfluorononaeicosyl, perfluorocycloeicosyl, perfluorophenyl, perfluorobenzyl, perfluoroxylyl, perfluoromesitylenyl, operfluorocumyl, perfluoronaphthanil, perfluorodecanyl, fluorodichloromethyl, 1,1-dichloro-1-fluoroethyl, 1-bromo-2-fluoroethyl, 1,1-difluoroethyl, bromotetrafluoropropyl, octabutylfluoro iodide, pentafluorophenyl, bromotetrafluorophenyl, chlorotetrafluorophenyl, tetrafluorophenyl iodide, tetrafluorophenyl, chlorotrifluorophenyl, dichlorotrifluorophenyl, bromotrifluorophenyl, dibromotrifluorophenyl, trifluorophenyl, chlorodifluorophenyl, dichlorodifluorophenyl, trichlorofluorophenyl, bromodifluorophenyl, dibromodifluorophenyl, tribromodifluorophenyl, difluorophenyl, chlorofluorophenyl, dichlorofluorophenyl, trichlorofluorophenyl, tetrachlorofluorophenyl, bromofluorophenyl, dibromofluorophenyl, tribromofluorophenyl, tetrabromofluorophenyl, hexafluoroxylyl, trifluoromethylnaphthyl, di-(trifluoromethyl)-naphthyl, trifluoromethyldecalyl, di-(trifluoromethyl)-decalyl, chloromethyl, chloroethyl, chloropropyl, chloroisopropyl, chlorocyclopropyl, chlorobutyl, chloroisobutyl, chloro-tert-butyl, chlorocyclobutyl, chloropentyl, chloroisopentyl chloroneopentyl, chlorocyclopentyl, chlorohexyl, chloroisohexyl, chlorocyclohexyl, chloroheptyl, chlorooctyl, chlorophenyl, chlorobenzyl, chloromesityl, chloroindenyl, chloronaphthyl, trichloroethyl, hexachloroisopropyl, pentachloropropyl, perchlorobutylethyl, perchloroethyl, perchlorodecylethyl, perchloroethylhexyl, perchlorobutylhexyl, perchlorohexylhexyl, perchlorooctylhexyl, perchloroisoamylethyl, perchloroisononylethyl, perchloroisopropylhexyl, perchloroisoamylhexyl, perchloroisoheptylhexyl, perchloroisononylhexyl, tetrachloropropyl, octachloropentyl, dodecachloroheptyl, hexadecachlorononyl, bis(trichloromethyl)propyl, hexachlorobutyl, octachloropropyl, perchlorobutyl, octachlorocyclobutyl, perchloropentyl, perchlorocyclopentyl, perchlorohexyl, perchlorocyclohexyl, perchloroheptyl, perchlorocycloheptyl, perchlorooctyl, perchlorocyclooctyl, perchlorononyl, perchlorocyclononyl, perchlorodecyl, perchlorocyclodecyl, perchloroundecyl, perchlorocycloundecyl, perchlorododecyl, perchlorocyclododecyl, perchlorotridecyl, perchlorocyclotridecyl, perchlorotetradecyl, perchlorocyclotetradecyl, perchloropentadecyl, perchlorocyclopentadecyl, perchlorohexadecyl, perchlorocyclohexadecyl, perchloroheptadecyl, perchlorocycloheptadecyl, perchlorooctadecyl, perchlorocyclooctadecyl, perchlorononadecyl, perchlorocyclononadecyl, perchloronanaeicosyl, perchlorocyclononaeicosyl, perchlorophenyl, perchlorobenzyl, perchloroxylyl, perchloromesitylenyl, perchlorochromyl, perchloronaphthyl, perchlorodecalyl, 1,1-dichloroethyl, pentachlorophenyl, tetrachlorophenyl, trichlorophenyl, dichlorophenyl, hexachloroxylyl, trichloromethylnaphthyl, di-(trichloromethyl)-naphthyl, trichloromethyldecalyl, di-(trichloromethyl)-decalyl, bromomethyl, bromoethyl, bromopropyl, bromoisopropyl, bromocyclopropyl, bromobutyl, bromoisobutyl, bromo-tert-butyl, bromocyclobutyl, bromopentyl, bromoisopentyl, bromoneopentyl bromocyclopentyl, bromohexyl, bromoisohexyl, bromocyclohexyl, bromoheptyl, bromoctyl, bromophenyl, bromobenzyl, bromomesityl, bromoindenyl, bromonaphthyl, tribromoethyl, hexabromoisopropyl, pentabromopropyl, perbromobutylethyl, perbromoethyl, perbromodecylethyl, perbromoethylhexyl, perbromobutylhexyl, perbromohexylhexyl, perbromooctylhexyl, perbromoisoamylethyl, perbromoisononylethyl, perbromoisopropylhexyl, perbromoisoamylhexyl, perbromoisoheptylhexyl, perbromoisononylhexyl, tetrabromopropyl, octabromopentyl, dodecabromoheptyl, hexadecabromononyl, bis(tribromomethyl)propyl, hexabromobutyl, octabromopropyl, perbromobutyl, octabromocyclobutyl, perbromopentyl, perbromocyclopentyl, perbromohexyl, perbromocyclohexyl, perbromoheptyl, perbromocycloheptyl, perbromoctyl, perbromocyclooctyl, perbromononyl, perbromocyclononyl, perbromodecyl, perbromocyclodecyl, perbromoundecyl, perbromocycloundecyl, perbromododecyl, perbromocyclododecyl group perbromotridecyl, perbromocyclotridecyl, perbromotetradecyl, perbromocyclotetradecyl, perbromopentadecyl, perbromocyclopentadecyl, perbromohexadecyl, perbromocyclohexadecyl, perbromoheptadecyl, perbromocycloheptadecyl, perbromoctadecyl, perbromocyclooctadecyl, perbromononadecyl, perbromocyclononadecyl, perbromononaeicosyl, perbromocyclononaeicosyl, perbromophenyl, perbromobenzyl, perbromoxylyl, perbromomesitylenyl, perbromochromyl, perbromonaphthyl, perbromodecalyl, 1,1-dibromoethyl, pentabromophenyl, tetrabromophenyl, tribromophenyl, dibromophenyl, hexabromoxylyl, tribromomethylnaphthyl, di-(tribromomethyl)-naphthyl, tribromomethyldecalyl, di-(tribromomethyl)-decalyl group and the like.

$R^8$ in each of the above formulae is the same as $R^4$ or a $C_1$–$C_{30}$, preferably a $C_1$–$C_{20}$, more preferably a $C_1$–$C_{12}$ hydrocarbon group. Where there are a plurality of $R^8$ in the molecule, they may be the same or different and may exemplarily include alkyl groups such as methyl, ethyl, propyl, isopropyl, cyclopropyl, butyl, isobutyl, tert-butyl, pentyl, isopentyl, neopentyl, cyclopentyl, hexyl, isohexyl, cyclohexyl, heptyl, octyl, decyl and dodecyl; alkenyl groups such as vinyl and allyl; aryl groups such as phenyl, tolyl, xylyl, mesityl, indenyl and naphthyl; aralkyl groups such as benzyl, trityl, phenethyl, styryl, benzhydryl, phenylbutyl and phenylpropyl and neophyl groups. Each of these hydrocarbon groups may be of branched-chain.

$R^9$ is the same as $R^8$ or a hydrogen atom. $R^{10}$ is hydrogen or halogen such as fluorine, chlorine, bromine and iodine.

The formula X compound exemplarily includes 3-perfluorohexyl-1,2-epoxypropane, 3-perfluorooctyl-1,2-epoxypropane, 3-perfluorodecyl-1,2-epoxypropane, 3-(perfluoro-3-methylbutyl)-1,2-epoxypropane, 3-(perfluoro-5-methylhexyl)-1,2-epoxypropane, 3-(perfluoro-7-methyloctyl)-1,2-epoxypropane, 3-(perfluoro-9-methyldecyl)-1,2-epoxypropaney, 3-perchlorohexyl-1,2-epoxypropane, 3-perchlorooctyl-1,2-epoxypropane, 3-perchlorodecyl-1,2-epoxypropane, 3-(perchloro-3-methylbutyl)-1,2-epoxypropane, 3-(perchloro-5-methylhexyl)-1,2-epoxypropane, 3-(perchloro-7-methyloctyl)-1,2-epoxypropane, 3-(perchloro-9-methyldecyl)-1,2-epoxypropane, 3-perbromohexyl-1,2-epoxypropane, 3-perbromooctyl-1,2-epoxypropane, 3-perbromodecyl-1,2-epoxypropane, 3-(perbromo-3-methylbutyl)-1,2-epoxypropane, 3-(perbromo-5-methylhexyl)-1,2-epoxypropane, 3-(perbromo-7-methyloctyl)-1,2-epoxypropane, 3-(perbromo-9-methyldecyl)-1,2-epoxypropane and the like.

The formula XI compound exemplarily includes 3-(2,2,3,3-tetrafluoropropoxy)-1,2-epoxypropane, 3-(1H,1H,5H-octafluoropentyloxy)-1,2-epoxypropane, 3-(1H,1H,7H-dodecafluoroheptyloxy)-1,2-epoxypropane, 3-(1H,1H,9H-hexadecafluorononyloxy)-1,2-epoxypropane, 3-(2,2,3,3-tetrachloropropoxy)-1,2-epoxypropane, 3-(1H,1H,5H-octachloropentyloxy)-1,2-epoxypropane, 3-(1H,1H,7H-dodecachloroheptyloxy)-1,2-epoxypropane, 3-(1H,1H,9H-hexadecachlorononyloxy)-1,2-epoxypropane, 3-(2,2,3,3-tetrabromopropoxy)-1,2-epoxypropane, 3-(1H,1H,5H-octabromopentyloxy)-1,2-epoxypropane, 3-(1H,1H,7H-dodecabromoheptyloxy)-1,2-epoxypropane, 3-(1H,1H,9H-hexadecabromononyloxy)-1,2-epoxypropane and the like.

The formula XII compound exemplarily includes 2-trifluoromethylfuran, 2-(1,1,1-trifluoroethyl)furan, 2-(2-trifluoromethyl-1,1,1-trifluoroethyl )furan, 2-trichloromethylfuran, 2-(1,1,1-trichloroethyl)furan, 2-(2-trichloromethyl-1,1,1-trichloroethyl )furan, 2-tribromomethylfuran, 2-(1,1,1-tribromoethyl)furan, 2-(2-tribromomethyl-1,1,1-tribromoethyl)furan and the like.

The formula XIII compound exemplarily includes 2-trifluoromethyltetrahydrofuran, 2-(1,1,1-trifluoroethyl)tetrahydrofuran, 2-(2-trifluoromethyl-1,1,1-trifluoroethyl)tetrahydrofuran, 2-trichloromethyltetrahydrofuran, 2-(1,1,1-trichloroethyl)tetrahydrofuran, 2-(2-trichloromethyl-1,1,1-trichloroethyl)tetrahydrofuran, 2-tribromomethyltetrahydrofuran, 2-(1,1,1-tribromoethyl)tetrahydrofuran, 2-(2-tribromomethyl-1,1,1-tribromoethyl)tetrahydrofuran and the like.

The formula XIV compound exemplarily includes 2-trifluoromethyltetrahydropyran, 2-(1,1,1-trifluoroethyl)tetrahydropyran, 2-(2-trifluoromethyl-1,1,1-trifluoroethyl)tetrahydropyran, 2-trichloromethyltetrahydropyran, 2-(1,1,1-trichloroethyl)tetrahydropyran, 2-(2-trichloromethyl-1,1,1-trichloroethyl)tetrahydropyran, 2-tribromomethyltetrahydropyran, 2-(1,1,1-tribromoethyl)tetrahydropyran, 2-(2-tribromomethyl-1,1,1-tribromoethyl)tetrahydropyran and the like.

The formula XV compound is suitably a tetrahydrofranylether derivative and specifically includes 2-(2',2',2'-trifluoroethoxy)-tetrahydrofuran, 2-(1'-methyl-2',2',2'-trifluoroethoxy)-tetrahydrofuran, 2-(1'-trifluoromethyl-2',2', 2'-trifluoroethoxy)-tetrahydrofuran, 2-(2',2',3',3',3'-pentafluoropropoxy)-tetrahydrofuran, 2-(6'-(perfluoroethyl)-hexyloxy)-tetrahydrofuran, 2-(1'H,1'H,-hexafluorobutoxy)-tetrahydrofuran, 2-(2'-(perfluorobutyl)-ethoxy)-tetrahydrofuran, 2-(2'-(perfluorobutyl)-hexyloxy)-tetrahydrofuran, 2-(2',2',2'-trichloroethoxy)-tetrahydrofuran, 2-(1'-methyl-2',2',2'-trichloroethoxy)- tetrahydrofuran, 2-(1'-trichloromethyl-2',2',2'-trichloroethoxy)-tetrahydrofuran, 2-(2',2',3',3',3'-pentachloropropoxy)-tetrahydrofuran, 2-(6'-(perchloroethyl)-hexyloxy)-tetrahydrofuran, 2-(1'H,1'H,-hexachlorobutoxy)-tetrahydrofuran, 2-(2'-(perchlorobutyl)-ethoxy)-tetrahydrofuran, 2-(2'-(perchlorobutyl)-hexyloxy)-tetrahydrofuran, 2-(2',2',2'-tribromoethoxy)-tetrahydrofuran, 2-(1'-methyl-2',2',2'-tribromoethoxy)-tetrahydrofuran, 2-(1'-tribromomethyl-2',2',2'-tribromoethoxy)-tetrahydrofuran, 2-(2',2',3',3',3'-pentabromopropoxy)-tetrahydrofuran, 2-(6'-(perbromoethyl)-hexyloxy)-tetrahydrofuran, 2-(1'H,1'H,-hexabromobutoxy)-tetrahydrofuran, 2-(2'-(perbromobutyl)-ethoxy)-tetrahydrofuran, 2-(2'-(perbromobutyl)-hexyloxy)-tetrahydrofuran and the like.

The formula XVI compound, suitably a tetrahydropyranylether derivative, specifically includes 2-(2',2',2'-trifluoroethoxy)-tetrahydropyran, 2-(1'-methyl-2',2',2'-trifluoroethoxy)-tetrahydropyran, 2-(1'-trifluoromethyl-2',2',2'-trifluoroethoxy)-tetrahydropyran, 2-(2',2',3',3',3'-pentafluoropropoxy)-tetrahydropyran, 2-(6'-(perfluoroethyl)-hexyloxy)-tetrahydropyran, 2-(1'H,1'H,-hexafluorobutoxy)-tetrahydropyran, 2-(2'-(perfluorobutyl)-ethoxy)-tetrahydropyran, 2-(2'-(perfluorobutyl)-hexyloxy)-tetrahydropyran, 2-(2',2',2'-trichloroethoxy)-tetrahydropyran, 2-(1'-methyl-2',2',2'-trichloroethoxy)-tetrahydropyran, 2-(1'-trichloromethyl-2',2',2'-trichloroethoxy)-tetrahydropyran, 2-(2',2',3',3',3'-pentachloropropoxy)-tetrahydropyran, 2-(6'-(perchloroethyl)-hexyloxy)-tetrahydropyran, 2-(1'H,1'H,-hexachlorobutoxy)-tetrahydropyran, 2-(2'-(perchlorobutyl)-ethoxy)-tetrahydropyran, 2-(2'-(perchlorobutyl)-hexyloxy)-tetrahydropyran, 2-(2',2',2'-tribromoethoxy)-tetrahydropyran, 2-(1'-methyl-2',2',2'-tribromoethoxy)-tetrahydropyran, 2-(1'-tribromomethyl-2',2',2'-tribromoethoxy)-tetrahydropyran, 2-(2',2',3',3',3'-pentabromopropoxy)-tetrahydropyran, 2-(6'-(perbromoethyl)-hexyloxy)-tetrahydropyran, 2-(1'H,1'H,-hexabromobutoxy)-tetrahydropyran, 2-(2'-(perbromobutyl)-ethoxy)-tetrahydropyran, 2-(2'-(perbromobutyl)-hexyloxy)-tetrahydropyran and the like.

The formula XVII compound is a halogen-containing ether compound specifically including 2,2,3,3,3-pentafluoropropyl-methylether, 2,2,3,3,3-pentafluoropropyl-1,1,2,2-tetrafluoroethylether, 1,1,2,2-tetrafluoroethylmethylether, 1,1,2-trifluoro-2-chloroethyl-2,2,2-trifluoroethylether, 1,1,3,3,3-pentafluoro-2-trifluoromethylpropylether, 2,2,2-trifluoroethylether, 2,2,2-trifluoroethylethylether, 2,2,2-trifluoroethylbutylether, 2,2,2-trifluoroethylbenzylether, 2,2,2-trifluoroethyltritylether, 2,2,3,3-pentafluoropropyltritylether, 6-(perfluoroethyl)-hexyltritylether, 1H,1H,-hexafluorobutyltritylether, 2-(perfluorobutyl)-ethyltritylether, 6-(perfluorobutyl)-hexyltritylether, 2-perfluorohexylethyltritylether, 2-perfluorooctylethyltritylether, 2,2,3,3,3-pentachloropropyl-methylether, 2,2,3,3,3-pentachloropropyl-1,1,2,2-tetrachloroethylether, 1,1,2,2-tetrachloroethylmethylether, 1,1,3,3,3-pentachloro-2-trichloromethylpropylether, 2,2,2-trichloroethylether, 2,2,2-trichloroethylethylether, 2,2,2-trichloroethylbutylether, 2,2,2-trichloroethylbenzylether, 2,2,2-trichloroethyltritylether, 2,2,3,3-pentachloropropyltritylether, 6-(perchloroethyl)-hexyltritylether, 1H,1H,-hexachlorobutyltritylether, 2-(perchlorobutyl)-ethyltritylether, 6-(perchlorobutyl)-hexyltritylether, 2-perchlorohexylethyltritylether, 2-perchlorooctylethyltritylether, 2,2,3,3,3-pentabromopropyl-methylether, 2,2,3,3,3-pentabromopropyl-1,1,2,2-tetrabromoethylether, 1,1,2,2-tetrabromoethylmethylether, 1,1,2-tribromo-2-chloroethyl-2,2,2-tribromoethylether, 1,1,3,3,3-pentabromo-2-tribromomethylpropylether, 2,2,2-tribromoethylether, 2,2,2-tribromoethylethylether, 2,2,2-tribromoethylbutylether, 2,2,2-tribromoethylbenzylether, 2,2,2-tribromoethyltritylether, 2,2,3,3-pentabromopropyltritylether, 6-(perbromoethyl)-hexyltritylether, 1H,1H,-hexabromobutyltritylether, 2-(perbromobutyl)-ethyltritylether, 6-(perbromobutyl)-hexyltritylether, 2-perbromohexylethyltritylether, 2-perbromooctylethyltritylether and the like.

The formula XVIII compound is a halogen-containing silylether including 2,2,2-trifluoroethyltrimethylsilylether, 2,2,3,3-pentafluoropropyltrimethylsilylether, 6-(perfluoroethyl)-hexyltrimethylsilylether, 1H,1H,-hexafluorobutyltrimethylsilylether, 2-(perfluorobutyl)-ethyltrimethylsilylether, 6-(perfluorobutyl)-hexyltrimethylsilylether, 2-perfluorohexylethyltrimethylsilylether, 2-perfluorooctylethyltrimethylsilylether, 2,2,2-trifluoroethyltriphenylsilylether, 2,2,3,3-pentafluoropropyltriphenylsilylether, 6-(perfluoroethyl)-hexyltriphenylsilylether, 1H,1H,-hexafluorobutyltriphenylsilylether, 2-(perfluorobutyl)-ethyltriphenylsilylether, 6-(perfluorobutyl)-hexyltriphenylsilylether, 2-perfluorohexylethyltriphenylsilylether, 2-perfluorooctylethyltriphenylsilylether, 2,2,2-trichloroethyltrimethylsilylether, 2,2,3,3-pentachloropropyltrimethylsilylether, 6-(perchloroethyl)-hexyltrimethylsilylether, 1H,1H,-hexachlorobutyltrimethylsilylether, 2-(perchlorobutyl)-ethyltrimethylsilylether, 6-(perchlorobutyl)-hexyltrimethylsilylether, 2-perchlorohexylethyltrimethylsilylether, 2-perchlorooctylethyltrimethylsilylether, 2,2,2-trichloroethyltriphenylsilylether, 2,2,3,3-pentachloropropyltriphenylsilylether, 6-(perchloroethyl)-hexyltriphenylsilylether, 1H,1H,-hexachlorobutyltriphenylsilylether, 2-(perchlorobutyl)-ethyltriphenylsilylether, 6-(perchlorobutyl)-hexyltriphenylsilylether, 2-perchlorohexylethyltriphenylsilylether, 2-perchlorooctylethyltriphenylsilylether, 2,2,2-tribromoethyltrimethylsilylether, 2,2,3,3-pentabromopropyltrimethylsilylether, 6-(perbromoethyl)-hexyltrimethylsilylether, 1H,1H,-hexabromobutyltrimethylsilylether, 2-(perbromobutyl)-ethyltrimethylsilylether, 6-(perbromobutyl)-hexyltrimethylsilylether, 2-perbromohexylethyltrimethylsilylether, 2-perbromooctylethyltrimethylsilylether, 2,2,2-tribromoethyltriphenylsilylether, 2,2,3,3-pentabromopropyltriphenylsilylether, 6-(perbromoethyl)-hexyltriphenylsilylether, 1H,1H,-hexabromobutyltriphenylsilylether, 2-(perbromobutyl)-ethyltriphenylsilylether, 6-(perbromobutyl)-hexyltriphenylsilylether, 2-perbromohexylethyltriphenylsilylether, 2-perbromooctylethyltriphenylsilylether and the like.

The formula XIX compound is an acetone derived acetal or a ketone derived ketal exemplariy including 2,2-dimethoxy-1,1,1-trifluoropropane, 2,2-diethoxy-1,1,1-trifluoropropane, 2,2-dimethoxy-1,1,1,3,3-hexafluoropropane, 2,2-diethoxy-1,1,1,3,3-hexafluoropropane, 1,1-dimethoxy-1-pentafluorophenylethane, 1,1-diethoxy-1- pentafluorophenylethane, dimethoxydipentafluorophenylmethane, diethoxydipentafluorophenylmethane, 2,2-dimethoxy-1,1,1-trichloropropane, 2,2-diethoxy-1,1,1-trichloropropane, 2,2-dimethoxy-1,1,1,3,3-hexachloropropane, 2,2-diethoxy-1,1,1,3,3-hexachloropropane, 1,1-dimethoxy-1-pentachlorophenylethane, 1,1-diethoxy-1-pentachlorophenylethane, dimethoxydipentachlorophenylmethane, diethoxydipentachlorophenylmethane and the like.

The formula XX compound is a an alcohol derived acetal or ketal exemplarily including 2,2-bis(2,2,2-trifluoroethoxy)-propane, 1,1-bis(2,2,2-trifluoroethoxy)-cyclohexane, 1,1-bis(2,2,2-trifluoroethoxy)-1-phenylethane, di(2,2,2-trifluoroethoxy)diphenylethane, di(2,2,2-trifluoroethoxy)phenylethane, 2,2-bis(2,2,2-trichloroethoxy)-propane, 1,1-bis(2,2,2-trichloroethoxy)-cyclohexane, 1,1-bis(2,2,2-trichloroethoxy)-1-phenylethane, di(2,2,2-trichloroethoxy)diphenylethane, di(2,2,2-trichloroethoxy)phenylethane, 2,2-bis(2,2,2-tribromoethoxy)-propane, 1,1-bis(2,2,2-tribromoethoxy)-cyclohexane, 1,1-bis(2,2,2-tribromoethoxy)-1-phenylethane, di(2,2,2-tribromoethoxy)diphenylethane, di(2,2,2-tribromoethoxy)phenylethane and the like.

The formula XXI compound is a carboxylic acid derived orthoester compound such as 1,1,1-trimethoxy-2,2,2-trifluoroethane, 1,1,1-triethoxy-2,2,2-trifluoroethane, 1,1,1-trimethoxy-2,2,2-trichloroethane, 1,1,1-triethoxy-2,2,2-trichloroethane, 1,1,1-trimethoxy-2,2,2-tribromoethane, 1,1,1-triethoxy-2,2,2-tribromoethane and the like.

The formula XXII compound is an alcohol derived orthoester such as 1,1,1-tri(2,2,2-trifluoroethoxy)-ethane, 1,1,1-tri(2,2,2-trichloroethoxy)-ethane, 1,1,1-tri(2,2,2-tribromoethoxy)-ethane, 1,1,1-tri(2,2,2-triiodoethoxy)-ethane and the like.

The formula XXIII compound is a hydrocarbon having bonded thereto one or more halogen atoms, exemplarily including perfluorohexane, perfluorocyclohexane, perfluoroheptane, perfluoromethylcyclohexane, perfluorooctane, 1-bromoheptadecafluorooctane, perfluorododecane, perfluoro-2,7-dimethyloctane, perfluoro-2,11-dimethyldodecane, tribromofluoromethane, dibromofluoromethane, 1-bromo-2-fluoromethane, 1,2-dibromo-1,1-difluoroethane, 1,1,1-trichlorotrifluoroethane, 1,1,1,3-tetrachlorotetrafluoropropane, 1,2-dibromohexafluoropropane, 1,1,3,4-tetrachlorohexafluorobutane, 1,1,1,3,5,-hexachlorooctafluorohexane, 1,1,3,5,6-pentachlorononafluorohexane, hexafluorobenzene, chloropentafluorobenzene, bromopentafluorobenzene, pentafluorobenzene, dichlorotetrafluorobenzene, dibromotetrafluorobenzene, tetrafluorobenzene, trichlorotrifluorobenzene, tribromotrifluorobenzene, trifluorobenzene, tetrachlorodifluorobenzene, tetrabromodifluorobenzene, 1,2-difluorobenzene, 1,3-difluorobenzene, 1,4-difluorobenzene, fluorobenzene, perfluorotoluene, perfluoromethylcyclohexane, trifluoromethylbenzene, benzylfluoride, 1,2-bistrifluoromethylbenzene, 1,3-bistrifluoromethylbenzene, 1,4-bistrifluoromethylbenzene, octafluoronaphthalene, perfluorodecalin, perfluoromethyldecalin, perfluorobiphenyl, dichloromethane, chloroform, 1,1-dichloroethane, 1,2-dichloroethane, 1,1,1-trichloroethane, 1,1,2-trichloroethane, 1,1-dichloropropane, 1,2-dichloropropane, 1,3-dichloropropane, perchlorohexane, perchloroheptan, perchloromethylcyclohexane, perchlorooctane, perchlorododecane, perchloro-2,7-dimethyloctane, perchloro-2,11-dimethyldodecane, hexachlorobenzene, pentachlorobenzene, tetrachlorobenzene, trichlorobenzene, dichlorobenzene, chlorobenzene, perchlorotoluene, perchloromethylcyclohexane, trichloromethylbenzene, benzylchloride, bistrichloromethylbenzene, octachloronaphthalene, perchlorodecalin, perchlorobiphenyl, perbromohexane, perbromoheptan, perbromomethylcyclohexane, perbromooctane, perbromododecane, perbromo-2,7-dimethyloctane, perbromo-2,11-dimethyldodecane, hexabromobenzene, pentabromobenzene, tetrabromobenzene, tribromobenzene, dibromobenzene, bromobenzene, perbromotoluene, perbromomethylcyclohexane, tribromomethylbenzene, benzylchloride, bistribromomethylbenzene, octabromonaphthalene, perbromodecalin, perbromobiphenyl and the like.

Particularly preferred are formula XVII, XVIII and XXIII compounds, more specifically these including 3-perfluorohexyl-1,2-epoxypropane, 2-trifluoromethylfuran, 2-trifluoromethyltetrahydrofuran, 2-trifluoromethyltetrahydropyran, 2,2,2-trifluoroethylbenzylether, 2,2,2-trifluoroethyltritylether, 2,2,3,3-pentafluoropropyltritylether, 1H,1H,-hexafluorobutyltritylether, 2,2,2-trifluoroethyltriphenylsilylether, 2,2,3,3-pentafluoropropyltriphenylsilylether, 1H,1H,-hexafluorobutyltriphenylsilylether, 2,2-dimethoxy-1,1,1-trifluoropropane, 2,2-diethoxy-1,1,1-trifluoropropane, 2,2-dimethoxy-1,1,1,3,3,3-hexafluoropropane, 2,2-diethoxy-1,1,1,3,3,3-hexafluoropropane, 2,2-bis(2,2,2-trifluoroethoxy)propane, 1,1-bis(2,2,2-trifluoroethoxy)-cyclohexane, 1,1,1-trimethoxy-2,2,2-trifluoroethane, 1,1,1-triethoxy-2,2,2-trifluoroethane, hexafluorobenzene, 1,2-difluorobenzene, monofluorobenzene, perfluorotoluene, trifluorobenzene, 1,2-bistrifluoromethylbenzene, 1,3-bistrifluoromethylbenzene, 1,4-bistrifluoromethylbenzene, perfluorodecalin, perfluoromethyldecalin, dichloromethane, chloroform, 1,1-dichloroethane, 1,2-dichloroethane, 1,1,1-trichloroethane, 1,1,2-trichloroethane, 2-(2',2',2'-trifluoroethoxy)-tetrahydrofuran, 2-(1'-methyl-2',2',2'-trifluoroethoxy)-tetrahydrofuran, 2-(1'-trifluoromethyl-2',2', 2'-trifluoroethoxy)-tetrahydrofuran, 2-(2',2',2'-trifluoroethoxy)-tetrahydropyran, 2-(1'-methyl-2',2',2'-trifluoroethoxy)-tetrahydropyran, 2-(1'-trifluoromethyl-2',2', 2'-trifluoroethoxy)-tetrahydropyran and the like.

(2) Oxoacid and salts thereof (Db)

Compounds of this category designate an acid or its salt having a group containing an oxygen atom or a hydroxo OH coordinated with a metal or nonmetal such as phosphorus, silicon, boron, selenium, sulfur, nitrogen, tellurium, cobalt, bromine, chlorine, manganese, chromium, zinc, iron, tungsten, molybdenum vanadium, niobium, tantalum, etc. The term oxoacid also embraces peroxoacids having $O_2$ coordinated in place of oxygen atom as well as isopolyacids and heteropolyacids having a plurality of condensed acid molecules. It further refers to an orthoacid having a central element oxidized to a standard degree, a peroxide in higher oxidative condition, and a sub- and a hypo-acid in lower oxidative condition. Each of such oxoacids may contain crystal water, coordinated water, lattice water, structural water and adsorption water.

Specific examples of oxoacids useful the purpose of the invention include phosphoric acid, phosphorous acid, hypophosphorous acid, silicic acid, boric acid, arsenic acid, arsenious acid, selenic acid, sulfuric acid, nitric acid, nitrous acid, iodic acid, periodic acid, hypoiodous acid, hydrochloric acid, perchloric acid, chlorous acid, hypochlorous acid, manganic acid, permanganic acid, chromic acid, tungstic acid, molybdic acid, vanadic acid and hexahydroxoantimonic acid. Among which phosphoric acid, periodic acid, tungstic acid and molybdic acid are preferred.

Salts of such oxoacids include alkali metal salts of which countercation is an alkali metal such as sodium, potassium and cesium, quaternary ammonium salts of which countercation is ammonium or tetrabutylammonium and metal salt of which countercation is silver and palladium and further specifically include $Na_3PO_4$, $NaH_2PO_4$, $NaIO_4$, $KIO_4$, $NaClO_4$, $KClO_4$, $AgClO_4$, $Na_2MoO_4$, $Na_2WO_4$.

Such heteropolyacids and salts thereof may be of Keggin, Dowson or Anderson structure, of which Keggin is preferred, and may contain crystal water, coordinated water, lattice water adsorption water and structural water usually in an amount of less than 1000 mols, preferably less than 100 mols, more preferably about 1–50 mols per mol of heteropolyacid or salt thereof.

Heteropolyanion in the heteropolyacid is represented by the formula:

$$[X_pM_aO_z]^{m-} \qquad \ldots \text{(XXVIII)}$$

wherein X is a hetero atom selected from the group of P, Si, B, Ge, As, Se, Co, I, Mn, Cu, Zn, Cr, Fe and Al; M is a ligand selected from the group of W, Mo, V, Nb and Ta; p is an integer of $1 \leq p \leq 4$; a is an integer of $1 \leq a \leq 18$; z is an integer of $1 \leq z \leq 62$; and m is an integer of $1 \leq m \leq 15$.

The above heteropolyanion preferably contains one or more of P, Si and Ge as the heteroatom and one or more of W, Mo and V as the ligand. The above a is preferably 12, the value z is preferably 40 and the value m is preferably of dependent upon the type of heteroatom and ligand present.

Specific examples of heteropolyacids containing preferred heteropolyanions are $H_3PW_{12}O_{40}$, $H_4SiW_{12}O_{40}$, $H_4GeW_{12}O_{40}$, $H_5BW_{12}O_{40}$, $H_3PW_{11}MoO_{40}$, $H_3PW_{10}Mo2O_{40}$, $H_4SiW_{11}MoO_{40}$, $H_4SiW_{10}Mo_2O_{40}$, $H_3PMo_{12}O_{40}$, $H_4SiMo_{12}O_{40}$, $H_6P_2W_{18}O_{62}$, $H_6P_2Mo_{18}O_{62}$, $H_7SiW_{18}O_{62}$, $H_7SiMo_{18}O_{62}$, $H_3PMo_6W_6O_{40}$, $H_5PMo_{10}V_2O_{40}$, $H_4PW_{11}VO_{40}$, $H_5PMo_5W_5V_2O_{40}$, $H_4SiMo_{12}O_{40}$, $H_4SiMo_6W_6O_{40}$, $H_6SiMo_{10}V_2O_{40}$, $H_5SiW_{11}VO_{40}$ and $H_6SiMo_5W_5V_2O_{40}$.

The countercations, that may be present when a salt of the heteropolyacid is formed, include an alkaline metal ion such as sodium, potassium and cesium, a quaternary ammonium ion such as ammonium ion and tetrabutyl ammonium and a metal ion such as silver and palladium. Suitable examples of heteropolyacid salts include $Na_3PW_{12}O_{40}$, $K_3PW_{12}O_{40}$, $K_4SiW_{12}O_{40}$ and $Cs_{2.5}H_{0.5}PW_{12}O_{40}$.

The isopolyacid and its salts according to the invention exemplarily include $H_6Mo_7O_{24}$, $(NH_4)_6Mo_7O_{24}$, $Na_6Mo_2O_{24}$, $(NH_4)_4Mo_8O_{26}$, $Na_4Mo_8O_{26}$, $H_8W_{12}O_{40}$, $(NH_4)_8W_{12}O_{40}$, $Na_8W_{12}O_{40}$, $H_6W_6O_{21}$, $(NH_4)_6W_6O_{21}$, $Na_6W_6O_{21}$, $H_{10}W_{12}O_{41}$, $(NH_4)_{10}W_{12}O_{41}$, $Na_{10}W_{12}O_{41}$, $H_6W_{12}O_{39}$, $(NH_4)_6W_{12}O_{39}$ and $Na_6W_{12}O_{39}$.

It has been found that particularly useful among the foregoing component Db are $H_2WO_4$, $H_2MoO_4$, $H_3PW_{12}O_{40}$, $H_4SiW_{12}O_{40}$, $H_3PMo_{12}O_{40}$ and $H_4SiMo_{12}O_{40}$.

(3) Sulfonic acid and derivative thereof (Dc)

The term derivative as used herein designates sulfonates, sulfonic acid esters, sulfonamides and sulfonic halides.

The sulfonic acid referred to herein includes monosulfonic acid and disulfonic acid such as a $C_1$–$C_{20}$, preferably a $C_1$–$C_{12}$ alkyl sulfonic acid and alkyl disulfonic acid, a $C_2$–$C_{20}$, preferably a $C_2$–$C_{12}$ alkenyl sulfonic acid and alkenyl disulfonic acid, $C_6$–$C_{20}$, preferably a $C_6$–$C_{12}$ aryl sulfonic acid, aryl disulfonic acid, halogen-substituted alkyl sulfonic acid, halogen-substituted alkyl disulfonic acid, halogen-substituted aryl sulfonic acid and halogen-substituted aryl disulfonic acid, more specifically including methanesulfonic acid, ethanesulfonic acid, propanesulfonic acid, butanesulfonic acid, pentanesulfonic acid, hexanesulfonic acid, ethylenesulfonic acid, 1-propene-1-sulfonic acid, benzenesulfonic acid, o-toluenesulfonic acid, m-toluenesulfonic acid, p-toluenesulfonic acid, m-xylene-4-sulfonic acid, o-xylene-4-sulfonic acid, m-chlorobenzenesulfonic acid, p-chlorobenzenesulfonic acid, 2,4-dichlorobenzenesulfonic acid, p-bromobenzenesulfonic acid, naphthalenesulfonic acid, methanedisulfonic acid (methionic acid), 1,1-ethanedisulfonic acid, 1,2-ethanedisulfonic acid, 1,3-propanedisulfonic acid and trifluoromethanesulfonic acid.

The sulfonate includes such as a $C_1$–$C_{20}$, preferably a $C_1$–$C_{12}$ alkyl sulfonate and alkyl disulfonate, a $C_2$–$C_{20}$, preferably a $C_2$–$C_{12}$ alkenyl sulfonate and alkenyl disulfonate, $C_6$–$C_{20}$, preferably a $C_6$–$C_{12}$ aryl sulfonate, aryl disulfonate, halogen-substituted alkyl sulfonate, halogen-substituted alkyl disulfonate, halogen-substituted aryl sulfonate and halogen-substituted aryl disulfonate, more specifically including sodium methanesulfonate potassium methanesulfonate, magnesium methanesulfonate, calcium methanesulfonate, sodium ethanesulfonate, potassium ethanesulfonate, magnesium ethanesulfonate, calcium ethanesulfonate, sodium propanesulfonate, potassium propanesulfonate, magnesium propanesulfonate, calcium propanesulfonate, sodium butanesulfonate, potassium butanesulfonate, magnesium butanesulfonate, calcium butanesulfonate, sodium ethylenesulfonate, potassium ethylenesulfonate, magnesium ethylenesulfonate, calcium ethylenesulfonate, potassium 1-propene-1-sulfonate, sodium 1-propene-1-sulfonate, magnesium 1-propene-1-sulfonate, calcium 1-propene-1-sulfonate, potassium benzeneesulfonate, sodium benzeneesulfonate, magnesium benzeneesulfonate, calcium benzeneesulfonate, sodium o-toluenesulfonate, potassium o-toluenesulfonate, magnesium o-toluenesulfonate, calcium o-toluenesulfonate, potassium m-toluenesulfonate, sodium m-toluenesulfonate, magnesium m-toluenesulfonate, calcium m-toluenesulfonate, sodium p-toluenesulfonate, potassium p-toluenesulfonate, magnesium p-toluenesulfonate, calcium p-toluenesulfonate, magnesium m-xylene-4-sulfonate, calcium m-xylene-4-sulfonate, sodium o-xylene-4-sulfonate, potassium o-xylene-4-sulfonate, magnesium o-xylene-4-sulfonate, calcium o-xylene-4-sulfonate, sodium m-chlorobenzenesulfonate, potassium m-chlorobenzenesulfonate, magnesium m-chlorobenzenesulfonate, calcium m-chlorobenzenesulfonate, sodium p-chlorobenzenesulfonate, potassium p-chlorobenzenesulfonate, magnesium p-chlorobenzenesulfonate, calcium p-chlorobenzenesulfonate, 2,4-dichlorobenzenesulfonate, potassium 2,4-dichlorobenzenesulfonate, magnesium 2,4-dichlorobenzenesulfonate, calcium 2,4-dichlorobenzenesulfonate, sodium p-bromobenzenesulfonate, potassium p-bromobenzenesulfonate, magnesium p-bromobenzenesulfonate, calcium p-bromobenzenesulfonate, sodium trifluoromethanesulfonate, calcium trifluoromethanesulfonate, potassium trifluoromethanesulfonatee, magnesium trifluoromethanesulfonate, silver trifluoromethanesulfonate, sodium methionate, potassium methionate, calcium methionate and magnesium methionate.

The sulfonic acid ester includes a $C_1$–$C_2$ alkylester of a $C_1$–$C_{12}$ alkyl sulfonic acid and alkyl disulfonic acid, a $C_1$–$C_2$ alkylester of a $C_2$–$C_{20}$, preferably a $C_2$–$C_{12}$ alkenyl sulfonic acid alkenyl disulfonic acid, a $C_1$–$C_2$ alkylester of a $C_6$–$C_{20}$, preferably a $C_6$–$C_{12}$ aryl sulfonic acid and aryl disulfonic acid, a $C_1$–$C_2$ alkylester of halogen-substituted alkyl sulfonic acid and halogen-substituted alkyl disulfonic acid, and a $C_1$–$C_2$ alkylester of halogen-substituted aryl sulfonic acid and halogen-substituted aryl disulfonic acid. Suitable sulfonic ester examples are methyl methanesulfonate, methyl ethanesulfonate, methyl benzenesulfonate, methyl paratoluenesulfonate, methyl trifluoromethanesulfonate, ethyl methanesulfonate, ethyl ethanesulfonate, ethyl benzenesulfonate, ethyl paratoluenesulfonate, ethyl trifluoromethanesulfonate, dimethyl methionate, diethyl methionate and the like.

The sulfonamide includes such as a $C_1$–$C_{20}$, preferably a $C_1$–$C_{12}$ alkyl sulfonamide and alkyl disulfonamide, a $C_2$–$C_{20}$, preferably a $C_2$–$C_{12}$ alkenyl sulfonamide and alkenyl disulfonamide, a $C_6$–$C_{20}$, preferably a $C_2$–$C_{12}$ aryl sulfonamide, aryl disulfonamide, halogen-substituted alkyl sulfonamide, halogen-substituted alkyl disulfonamide, halogen-substituted aryl sulfonamide and halogen-substituted aryl disulfonamide, more specifically including methane sulfonamide, ethane sulfonamide, benzene sulfonamide, paratoluene sulfonamide, trifluoro sulfonamide, diamide methionate and the like.

The sulfonic halide includes such as a $C_1$–$C_{20}$, preferably a $C_1$–$C_{12}$ halide of alkyl sulfonic acid and alkyl disulfonic acid, a $C_2$–$C_{20}$, preferably a $C_2$–$C_{12}$ halide of alkenyl sulfonic acid and alkenyl disulfonic acid, $C_6$–$C_{20}$, preferably a $C_6$–$C_{12}$ halide of aryl sulfonic acid and aryl disulfonic acid, halide of halogen-substituted alkyl sulfonic acid and halogen-substituted alkyl disulfonic acid, halide of halogen-substituted aryl sulfonic acid and halogen-substituted aryl disulfonic acid, more specifically including fluoride methanesulfonate, fluoride ethanesulfonate, fluoride benzenesulfonate, fluoride paratoluenesulfonate, fluoride trifluoromethanesulfonate, chloride methanesulfonate, chloride ethanesulfonate, chloride benzenesulfonate, chloride paratoluenesulfonate, chloride trifluoromethanesulfonate, dichloride methionate and the like.

Particularly preferred among the recited components (Dc) are monosulfonic acids such as methanesulfonic acid, para-toluenesulfonic acid and trifluoromethanesulfonic acid.

(4) Compounds (Dd) of the formulae

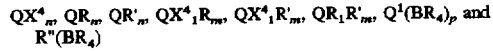

wherein Q is an element selected from the group of magnesium, titanium, zirconium, boron and tin; Q1 is an element selected from the group of lithium, sodium, potassium, calcium and zinc; X4 is halogen atom or hydrogen atom; R is a $C_1$–$C_{12}$, preferably a $C_1$–$C_8$ hydrocarbon group, R' is a $C_1$–$C_{12}$, preferably a $C_1$–$C_8$ oxygen-containing hydrocarbon group, R" is a $C_1$–$C_{20}$, preferably a $C_6$–$C_{12}$ hydrocarbon group or ammonium group, n is a valence of Q, l,m are a natural number that satisfied n=l+m, and p is a valence of $Q^1$.

The hydrocarbon group and oxygen containing hydrocarbon group in each of the above formulae includes alkyl group, aryl group, aralkyl group, cyclopolyenyl group, alkoxy group, aryloxy group and acyloxy group such as methyl group, methoxy group, ethyl group, ethoxy group, propyl group, propoxy group, isopropyl group, isopropoxy group, butyl group, butoxy group, isobutyl group, pentyl group, cyclopentyl group, hexyl group, cyclohexyl group, phenyl group, phenoxy group, tolyl group, xylyl group, benzyl group, trityl group, cycloheptatolyenyl group (cycloheptatolyenium cation), acetoxy group, formyloxy group, propionyloxy group, butyryloxy group, valeryloxy group and lauroyloxy group. Halogen atoms may be fluorine, chlorine, bromine and iodine, but fluorine and chlorine are preferred. Ammonium groups (ammonium cation) include trialkylammonium groups and anilinium groups (anilinium cation) such as trimethyl ammonium, triethylammonium and tributylammonium. In the case where Q is titanium or zirconium, its valence is preferably 4.

Compounds eligible for use as compound (D) are $MgR^4{}_2$, $R^4MgX$, $MgX_2$, $Ti(OR^4)_4$, $Ti(OR^4)_3X$, $Ti(OR^4)_2X_2$, $Ti(OR^4)X_3$, $TiX_4$, $Zr(OR^4)_4$, $Zr(OR^4)_3X$, $Zr(OR^4)_2X_2$, $Zr(OR^4)X_3$, $ZrX_4$, $ZnR^4{}_2$, $ZnX_2$, $BX_3$, $Sn(OR^4)_4$, $SnR^4{}_4$, $SnR^4{}_3H$, $SnR^4{}_3X$, $SnR^4{}_3(OR)$, $SnR^4{}_2X_2$, $SnR^4{}_2(OR^4)_2$, $SnR^4{}_2(OOCR^4)_2$, $Li(BR^4{}_4)$, $Na(BR^4{}_4)$, $K(BR^4{}_4)$, $Ca(BR^4{}_4)_2$, $Zn(BR^4{}_4)_2$ and $R^5(BR^4{}_4)$ wherein X is halogen atom, $R^4$ is a $C_1$–$C_8$ alkyl group or aryl group, $R^5$ is a $C_6$–$C_{20}$ alkyl group and a $C_1$–$C_8$ trialkylammonium group or anilinium group (aniliniumcation).

A range of useful components (D) more specifically and exemplarily covers magnesium chloride, titanium chloride (IV), tetramethoxytitanium, tetraethoxytitanium, tetrapropoxytitanium, tetraisopropoxytitanium, tetrabutoxytitanium, zirconium chloride(IV), tetramethoxyzirconium, tetraethoxyzirconium, tetrapropoxyzirconium, tetraisopropoxyzirconium, tetrabutoxyzirconium, zinc chloride, dimethylzinc, diethylzinc, diphenylzinc, boron trifluoride, hexabutylditin, tetramethyltin, tetraethyltin, tetrabutyltin, tetraphenyltin, tetraoctyltin, tributyltinacetate, tributyltinhydride, trimethyltinchloride, triethyltinchloride, triphenyltinchloride, tributyltinchloride, tripropyltinchloride, dibutyltinacetate, dioctyltinacetate, dibutyldimethoxytin, dibutyltindichloride, lithiumtetraphenyl borate, lithiumtetra(p-tolyl) borate, lithiumtetra(o-tolyl) borate, lithiumtetra(m-tolyl) borate, lithiumtetra(p-fluorophenyl) borate, lithiumtetra(o-fluorophenyl) borate, lithiumtetra(m-fluorophenyl) borate, lithiumtetra(3,5-difluorophenyl) borate, lithiumtetra(pentafluorophenyl) borate, sodiumtetraphenyl borate, sodiumtetra(p-tolyl) borate, sodiumtetra(o-tolyl) borate, sodiumtetra(m-tolyl) borate, sodiumtetra(p-fluorophenyl) borate, sodiumtetra(o-fluorophenyl) borate, sodiumtetra(m-fluorophenyl) borate, sodiumtetra(3,5-difluorophenyl) borate, potassiumtetraphenyl borate, potassiumtetra(p-tolyl) borate, potassiumtetra(o-tolyl) borate, potassiumtetra(m-tolyl) borate, potassiumtetra (p-fluorophenyl) borate, potassiumtetra(o-fluorophenyl) borate, potassiumtetra(m-fluorophenyl) borate, potassiumtetra(3,5-difluorophenyl) borate, potassiumtetra (pentafluorophenyl) borate, calciumbistetraphenyl borate, calciumbistetra(p-tolyl) borate, calciumbistetra(o-tolyl) borate, calciumbistetra(m-tolyl) borate, calciumbistetra(p-fluorophenyl) borate, calciumbistetra(o-fluorophenyl) borate, calciumbistetra(m-fluorophenyl) borate, calciumbistetra(3,5-difluorophenyl) borate, calciumbistetra (pentafluorophenyl) borate, zincbistetraphenyl borate, zincbistetra(p-tolyl) borate, zincbistetra(o-tolyl) borate, zincbistetra(m-tolyl) borate, zincbistetra(p-fluorophenyl) borate, zincbistetra(o-fluorophenyl) borate, zincbistetra(m-fluorophenyl) borate, zincbistetra(3,5-difluorophenyl) borate, zincbistetra(pentafluorophenyl) borate, trityltetraphenyl borate, trityltetra(p-tolyl) borate, trityltetra(o-tolyl) borate, trityltetra(m-tolyl) borate, trityltetra(p-fluorophenyl) borate, trityltetra(o-fluorophenyl) borate, trityltetra(m- fluorophenyl) borate, tritylteta(3,5-difluorophenyl) borate, tritylteta(pentafluorophenyl) borate, trimethyltetraphenyl borate, trimethyltetra(p-tolyl) borate, trimethyltetra(o-tolyl) borate, trimethyltetra(m-tolyl) borate, trimethyltetra(p-fluorophenyl) borate, trimethyltetra(o-fluorophenyl) borate, trimethyltetra(m-fluorophenyl) borate, trimethyltetra(3,5-difluorophenyl) borate, trimethyltetra(pentafluorophenyl) borate, triethyltetraphenyl borate, triethyltetra(p-tolyl) borate, triethyltetra(o-tolyl) borate, triethyltetra(m-tolyl) borate, triethyltetra(p-fluorophenyl) borate, triethyltetra(o-fluorophenyl) borate, triethyltetra(m-fluorophenyl) borate, triethyltetra(3,5-difluorophenyl) borate, triethyltetra (pentafluorophenyl) borate, tributyltetraphenyl borate, tributyltetra(p-tolyl) borate, tributyltetra(o-tolyl) borate, tributyltetra(m-tolyl) borate, tributyltetra(p-fluorophenyl) borate, tributyltetra(o-fluorophenyl) borate, tributyltetra(m-fluorophenyl) borate, tributyltetra(3,5-difluorophenyl) borate, tributyltetra(pentafluorophenyl) borate, aniliniumtetraphenyl borate, aniliniumtetra(p-tolyl) borate, aniliniumtetra(o-tolyl) borate, aniliniumtetra(m-tolyl) borate, aniliniumtetra(p-fluorophenyl)-borate, aniliniumtetra(o-fluorophenyl) borate, aniliniumtetra(m-fluorophenyl) borate, aniliniumtetra(3,5-difluorophenyl) borate, aniliniumtetra(pentafluorophenyl) borate and the like.

Among which lithiumtetraphenyl borate, sodiumtetraphenyl borate, potassiumtetraphenyl borate, calciumtetraphenyl borate, zincbistetraphenyl borate, trityltetraphenyl borate, trimethylammoniumtetraphenyl borate, triethylammoniumtetraphenyl borate, tributylammoniumtetraphenyl borate, aniliniumtetraphenyl borate, tetraisopropoxytitanium, tetrabutoxyzirconium, diethylzinc, tributyltinhydride, tributyltinchloride are preferred.

Compounds (D) may be used in the form of various complexes exemplarily including ethers complex, alcohols complex and sulfides complex of trifluoroboron such as trifluoroborondimethylether complex, trifluoroborondiethylether complex, trifluoroborontetrahydrofuran complex, trifluoroboronmethanol complex, trifluoroboronethanol complex, trifluoroboronpropanol complex and trifluoroboronmethylsulfide complex.

These complexes may be diluted, for ease of handling, by solvents such as hydrocarbon, ether, alcohol, phenol and the like. A typical example is a ROH solution of $Zr(OR)_4$.

Particularly preferred among the category of components (Dd) are tetraisopropoxytitanium, tetrabutoxyzirconium, diethylzinc, trifluoroborondiethylether complex, tributyltinhydride, tributyltinchloride, sodiumtetraphenyl borate and the like.

The inventive oligomerization catalyst may be prepared by contacting main components (A) through (D) together, in which instance there may be added other suitable components such as for example $C_4$–$C_{20}$, preferably $C_4$–$C_{12}$ non-aromatic hydrocarbon compounds having two or more carbon-carbon double bonds (hereinafter referred to as component (E)) thereby providing improved catalytic performance of the final catalyst product. Component (E) may be alkadienes cycloalkadienes and terpene unsaturated compounds, specifically including 1,3-butadiene, 2-methyl-1,3-butadiene, 1,3-pentadiene, 1,4-pentadiene, cyclopentadiene, 1,3-hexadiene, 1,5-hexadiene, 1,3-cyclohexadiene, 1,4-cyclohexadiene, 1,4-cyclooctadiene, 1,5-cyclooctadiene, norbornene, norbornadiene, ethylidenenorbornene, vinylnorbornene, dicyclopentadiene. One or more than two of the above compounds may be used. Among which 2-methyl-1,3-butadiene, 1,5-cyclooctadiene, vinylnorbornene and ethylidenenorbornene are preferred.

The main components (A)-(D) are contacted together usually in a closed reactor purged with nitrogen, argon or other inert gas in the presence of an organic solvent such as benzene, toluene, xylene, hexane, heptane, decane, dodecane, cyclohexane, chlorobenzene and the like. Contact temperature is in the range of minus 100° C.–200° C., preferably minus 50° C.–100° C., and contact time length is about from 1 second to 24 hours.

Each of components (A)–(D) may be contacted in any order but bearing in mind that the contact between components (A) and (C) should preferably be effected in the presence of component (B) to avoid the formation of precipitates.

The order in which components (A) through (D) and additionally (E) are contacted is shown by way of example and conveniently indicated by the arrows as follows:

1. (A)←(B)←(C)←(D)
2. (A)←(B)←(D)←(C)
3. (A)←(D)←(B)←(C)
4. (B)←(A)←(C)←(D)
5. (B)←(A)←(D)←(C)
6. (B)←(C)←(A)←(D)
7. (B)←(C)←(D)←(A)
8. (B)←(D)←(A)←(C)
9. (B)←(D)←(C)←(A)
10. (C)←(B)←(A)←(D)
11. (C)←(B)←(D)←(A)
12. (C)←(D)←(B)←(A)
13. (D)←(A)←(B)←(C)
14. (D)←(B)←(A)←(C)
15. (D)←(B)←(C)←(A)
16. (D)←(C)←(B)←(A)
17. Admix (A) and (B) to form component (J) and admix (C) and (D) to form component (F). Then, mix (J) with (F).
18. Admix (A) and (D) to form component (H) and admix (B) and (C) to form component (I). Then, mix (H) with (I).

1-1. (E)←(A)←(B)←(C)←(D)
1-2. (A)←(E)←(B)←(C)←(D)
1-3. (A)←(B)←(E)←(C)←(D)
1-4. (A)←(B)←(C)←(E)←(D)
1-5. (A)←(B)←(C)←(D)←(E)
2-1. (E)←(A)←(B)←(D)←(C)
2-2. (A)←(E)←(B)←(D)←(C)
2-3. (A)←(B)←(E)←(D)←(C)
2-4. (A)←(B)←(D)←(E)←(C)
2-5. (A)←(B)←(D)←(C)←(E)
3-1. (E)←(A)←(D)←(B)←(C)
3-2. (A)←(E)←(D)←(B)←(C)
3-3. (A)←(D)←(E)←(B)←(C)
3-4. (A)←(D)←(B)←(E)←(C)
3-5. (A)←(D)←(B)←(C)←(E)
4-1. (E)←(B)←(A)←(C)←(D)
4-2. (B)←(E)←(A)←(C)←(D)
4-3. (B)←(A)←(E)←(C)←(D)
4-4. (B)←(A)←(C)←(E)←(D)
4-5. (B)←(A)←(C)←(D)←(E)
5-1. (E)←(B)←(A)←(D)←(C)
5-2. (B)←(E)←(A)←(D)←(C)
5-3. (B)←(A)←(E)←(D)←(C)
5-4. (B)←(A)←(D)←(E)←(C)
5-5. (B)←(A)←(D)←(C)←(E)
6-1. (E)←(B)←(C)←(A)←(D)
6-2. (B)←(E)←(C)←(A)←(D)
6-3. (B)←(C)←(E)←(A)←(D)
6-4. (B)←(C)←(A)←(E)←(D)
6-5. (B)←(C)←(A)←(D)←(E)
7-1. (E)←(B)←(C)←(D)←(A)

7-2. (B)←(E)←(C)←(D)←(A)
7-3. (B)←(C)←(E)←(D)←(A)
7-4. (B)←(C)←(D)←(E)←(A)
7-5. (B)←(C)←(D)←(A)←(E)
8-1. (E)←(B)←(D)←(A)←(C)
8-2. (B)←(E)←(D)←(A)←(C)
8-3. (B)←(D)←(E)←(A)←(C)
8-4. (B)←(D)←(A)←(E)←(C)
8-5. (B)←(D)←(A)←(C)←(E)
9-1. (E)←(B)←(D)←(C)←(A)
9-2. (B)←(E)←(D)←(C)←(A)
9-3. (B)←(D)←(E)←(C)←(A)
9-4. (B)←(D)←(C)←(E)←(A)
9-5. (B)←(D)←(C)←(A)←(E)
10-1. (E)←(C)←(B)←(A)←(D)
10-2. (C)←(E)←(B)←(A)←(D)
10-3. (C)←(B)←(E)←(A)←(D)
10-4. (C)←(B)←(A)←(E)←(D)
10-5. (C)←(B)←(A)←(D)←(E)
11-1. (E)←(C)←(B)←(D)←(A)
11-2. (C)←(E)←(B)←(D)←(A)
11-3. (C)←(B)←(E)←(D)←(A)
11-4. (C)←(B)←(D)←(E)←(A)
11-5. (C)←(B)←(D)←(A)←(E)
12-1. (E)←(C)←(D)←(B)←(A)
12-2. (C)←(E)←(D)←(B)←(A)
12-3. (C)←(D)←(E)←(B)←(A)
12-4. (C)←(D)←(B)←(E)←(A)
12-5. (C)←(D)←(B)←(A)←(E)
13-1. (E)←(D)←(A)←(B)←(C)
13-2. (D)←(E)←(A)←(B)←(C)
13-3. (D)←(A)←(E)←(B)←(C)
13-4. (D)←(A)←(B)←(E)←(C)
13-5. (D)←(A)←(B)←(C)←(E)
14-1. (E)←(D)←(B)←(A)←(C)
14-2. (D)←(E)←(B)←(A)←(C)
14-3. (D)←(B)←(E)←(A)←(C)
14-4. (D)←(B)←(A)←(E)←(C)
14-5. (D)←(B)←(A)←(C)←(E)
15-1. (E)←(D)←(B)←(C)←(A)
15-2. (D)←(E)←(B)←(C)←(A)
15-3. (D)←(B)←(E)←(C)←(A)
15-4. (D)←(B)←(C)←(E)←(A)
15-5. (D)←(B)←(C)←(A)←(E)
16-1. (E)←(D)←(C)←(B)←(A)
16-2. (D)←(E)←(C)←(B)←(A)
16-3. (D)←(C)←(E)←(B)←(A)
16-4. (D)←(C)←(B)←(E)←(A)
16-5. (D)←(C)←(B)←(A)←(E)
17-1. (E)←(A)←(B)←(F)
17-2. (A)←(E)←(B)←(F)
17-3. (A)←(B)←(E)←(F)
17-4. (E)←(C)←(D)←(J)
17-5. (C)←(E)←(D)←(J)
17-6. (C)←(D)←(E)←(J)
18-1. (E)←(A)←(D)←(I)
18-2. (A)←(E)←(D)←(I)
18-3. (A)←(D)←(E)←(I)
18-4. (E)←(B)←(C)←(H)
18-5. (B)←(E)←(C)←(H)
18-6. (B)←(C)←(E)←(H)

Particularly preferred sequences are seen in the presence of (B) and (E) when contacting (A) with (C). Component (D) is preferably added after contact between (A) and (C).

In the preparation of the inventive catalyst, component (B) is added in an amount of usually 0.01–100 mole, preferably 0.1–10 mole, more preferably 0.5–5 mole per mol of component (A); component (C) in an amount of usually 0.01–10,000 mole, preferably 0.1–1,000 mole, more preferably 1–100 mole per mol of component (A); and component (D) in an amount of usually 0.001–100 mole, preferably 0.01–10 mole, more preferably 0.1–5 mole per mol of component (A).

Component (E) if used may be added in an amount not particularly restricted but usually in an amount of less than 1,000 mole, preferably 0.01–100 mole, more preferably 0.1–50 mole per mol of component (A).

Some of the preferred combinations of components (A) through (D) without or with additional component (E) according to the invention are exemplified below. Combinations with component (Da)

(1) Component (A):

nickel naphthenate, bis(acetoacetonate)nickel, nickel acetate, nickel 2-ethylhexanate Component (B):

triisopropylphosphine, tricyclohexylphosphine

Component (C):

diethylaluminumchloride, ethylaluminumsesquichloride

Component (D):

perfluorodecalin, perfluoromethyldecalin, 1,2-bistrifluoromethylbenzene, 1,3-bistrifluoromethylbenzene, 1,4-bistrifluoromethylbenzene, hexafluorobenzene Component (E):

2-methyl-1,3-butadiene, 1,5-cyclooctadiene, vinylnorbornene, ethylidenenorbornene (2) Component (A):

nickel naphthenate, bis(acetoacetonate)nickel, nickel acetate, nickel 2-ethylhexanate Component (B):

triphenylphosphine

Component (C):

diethylaluminumchloride, ethylaluminumsesquichloride

Component (D):

perfluorodecalin, perfluoromethyldecalin, 1,2-bistrifluoromethylbenzene, 1,3-bistrifluoromethylbenzene, 1,4-bistrifluoromethylbenzene, hexafluorobenzene Component (E):

2-methyl-1,3-butadiene, 1,5-cyclooctadiene, vinylnorbornene, ethylidenenorbornene (3) Component (A):

bis-(1,5-cyclooctadiene)-nickel

Component (B):

triisopropylphosphine, tricyclohexylphosphine

Component (C):

diethylaluminumchloride, ethylaluminumsesquichloride

Component (D):

perfluorodecalin, perfluoromethyldecalin, 1,2-bistrifluoromethylbenzene, 1,3-bistrifluoromethylbenzene, 1,4-bistrifluoromethylbenzene, hexafluorobenzene Component (E):

2-methyl-1,3-butadiene, 1,5-cyclooctadiene, vinylnorbornene, ethylidenenorbornene (4) Component (A):

bis-(1,5-cyclooctadiene)-nickel

Component (B):

triphenylphosphine

Component (C):

diethylaluminumchloride, ethylaluminumsesquichloride

Component (D):
perfluorodecalin, perfluoromethyldecalin, 1,2-bistrifluoromethylbenzene, 1,3-bistrifluoromethylbenzene, 1,4-bistrifluoromethylbenzene, hexafluorobenzene
Component (E):
2-methyl-1,3-butadiene, 1,5-cyclooctadiene, vinylnorbornene, ethylidenenorbornene
Combinations with component (Db)
(1) Component (A):
nickel naphthenate, bis(acetoacetonate)nickel, nickel acetate, nickel 2-ethylhexanate
Component (B):
triisopropylphosphine, tricyclohexylphosphine
Component (C):
diethylaluminumchloride, ethylaluminumsesquichloride
Component (D):
phosphorus tungstic acid, phosphorus molybdic acid, silicotungstic acid, silicomolybdic acid, tungstic acid, molybdic acid
Component (E):
2-methyl-1,3-butadiene, 1,5-cyclooctadiene, vinylnorbornene, ethylidenenorbornene
(2) Component (A):
nickel naphthenate, bis(acetoacetonate)nickel, nickel acetate, nickel 2-ethylhexanate
Component (B):
triphenylphosphine
Component (C):
diethylaluminumchloride, ethylaluminumsesquichloride
Component (D):
phosphorus tungstic acid, phosphorus molybdic acid, silicotungstic acid, silicomolybdic acid, tungstic acid, molybdic acid
Component (E):
2-methyl-1,3-butadiene, 1,5-cyclooctadiene, vinylnorbornene, ethylidenenorbornene
(3) Component (A):
bis-(1,5-cyclooctadiene)-nickel
Component (B):
triisopropylphosphine, tricyclohexylphosphine
Component (C):
diethylaluminumchloride, ethylaluminumsesquichloride
Component (D):
phosphorus tungstic acid, phosphorus molybdic acid, silicotungstic acid, silicomolybdic acid, tungstic acid, molybdic acid
Component (E):
2-methyl-1,3-butadiene, 1,5-cyclooctadiene, vinylnorbornene, ethylidenenorbornene
(4) Component (A):
bis-(1,5-cyclooctadiene)-nickel
Component (B):
triphenylphosphine
Component (C):
diethylaluminumchloride, ethylaluminumsesquichloride
Component (D):
phosphorus tungstic acid, phosphorus molybdic acid, silicotungstic acid, silicomolybdic acid, tungstic acid, molybdic acid
Component (E):
2-methyl-1,3-butadiene, 1,5-cyclooctadiene, vinylnorbornene, ethylidenenorbornene Combinations with component (Dc)
(1) Component (A):
nickel naphthenate, nickel 2-ethylhexanate, bis(acetoacetonate)nickel, nickel acetate, bis-(1,5-cyclooctadiene)-nickel
Component (B):
triisopropylphosphine, tricyclohexylphosphine
Component (C):
triethylaluminum, diethylaluminumchloride, ethylaluminumsesquichloride
Component (D):
trifluoromethanesulfonic acid
Component (E):
2-methyl-1,3-butadiene, 1,5-cyclooctadiene, vinylnorbornene, ethylidenenorbornene
(2) Component (A):
nickel naphthenate, nickel 2-ethylhexanate, bis(acetoacetonate)nickel, nickel acetate, bis-(1,5-cyclooctadiene)-nickel
Component (B):
triisopropylphosphine, tricyclohexylphosphine
Component (C):
triethylaluminum, diethylaluminumchloride, ethylaluminumsesquichloride
Component (D):
paratoluenesulfonic acid, sodium paratoluenesulfonate
Component (E):
2-methyl-1,3-butadiene, 1,5-cyclooctadiene, vinylnorbornene, ethylidenenorbornene
(3) Component (A):
nickel naphthenate, nickel 2-ethylhexanate, bis(acetoacetonate)nickel, nickel acetate, bis-(1,5-cyclooctadiene)-nickel
Component (B):
triphenylphosphine
Component (C):
triethylaluminum, diethylaluminumchloride, ethylaluminumsesquichloride
Component (D):
trifluoromethanesulfonic acid
Component (E):
2-methyl-1,3-butadiene, 1,5-cyclooctadiene, vinylnorbornene, ethylidenenorbornene
(4) Component (A):
nickel naphthenate, nickel 2-ethylhexanate, bis(acetoacetonate)nickel, nickel acetate, bis-(1,5-cyclooctadiene)-nickel
Component (B):
triphenylphosphine
Component (C):
triethylaluminum, diethylaluminumchloride, ethylaluminumsesquichloride
Component (D):
paratoluenesulfonic acid, sodium paratoluenesulfonate
Component (E):
2-methyl-1,3-butadiene, 1,5-cyclooctadiene, vinylnorbornene, ethylidenenorbornene Combinations with component (Dd)
(1) Component (A):
nickel naphthenate, nickel 2-ethylhexanate, bis(acetoacetonate)nickel, nickel acetate
Component (B):
triisopropylphosphine, tricyclohexylphosphine Component (C):
diethylaluminumchloride, ethylaluminumsesquichloride
Component (D):
magnesium chloride, titanium chloride(IV), tetraisopropoxytitanium, tetrabutoxyzirconium, fluoroboron (III) diethylether complex salt, triphenyltinchloride, dibutyltindichloride, sodiumtetraphenyl borate
Component (E):
2-methyl-1,3-butadiene, 1,5-cyclooctadiene, vinylnorbornene, ethylidenenorbornene (2) Component (A):
nickel naphthenate, nickel 2-ethylhexanate, bis(acetoacetonate)nickel, nickel acetate
Component (B):
triphenylphosphine
Component (C):
diethylaluminumchloride, ethylaluminumsesquichloride
Component (D):
magnesium chloride, titanium chloride (IV), tetraisopropoxytitanium, tetrabutoxyzirconium, fluoroboron (III) diethylether complex salt, triphenyltinchloride, dibutyltindichloride, sodiumtetraphenyl borate
Component (E):
2-methyl-1,3-butadiene, 1,5-cyclooctadiene, vinylnorbornene, ethylidenenorbornene (3) Component (A):
bis-(1,5-cyclooctadiene)-nickel
Component (B):
triisopropylphosphine, tricyclohexylphosphine
Component (C):
diethylaluminumchloride, ethylaluminumsesquichloride
Component (D):
magnesium chloride, titanium chloride (IV), tetraisopropoxytitanium, tetrabutoxyzirconium, fluoroboron (III) diethylether complex salt, triphenyltinchloride, dibutyltindichloride, sodiumtetraphenyl borate
Component (E):
2-methyl-1,3-butadiene, 1,5-cyclooctadiene, vinylnorbornene, ethylidenenorbornene (4) Component (A):
bis-(1,5-cyclooctadiene)-nickel
Component (B):
triphenylphosphine
Component (C):
diethylaluminumchloride, ethylaluminumsesquichloride
Component (D):
magnesium chloride, titanium chloride (IV), tetraisopropoxytitanium, tetrabutoxyzirconium, fluoroboron (III) diethylether complex salt, triphenyltinchloride, dibutyltindichloride, sodiumtetraphenyl borate
Component (E):
2-methyl-1,3-butadiene, 1,5-cyclooctadiene, vinylnorbornene, ethylidenenorbornene The process of the invention is characterized by the use of the above described catalysts for the oligomerization of α-olefins.

The α-olefins, i.e. the starting monomer, have a carbon number of 2–12, preferably 2–8, including ethylene, propylene, 1-butene, isobutene, 1-pentene, 1-hexene, 3-methyl-1-pentene, 4-methyl-1-pentene, 1-octene and 1-decene, of which ethylene and propylene are preferred and propylene is more particularly preferred.

The oligomerization catalyst may be varied in its concentration depending upon the mode of reaction employed which may be solution reaction, gas-phase reaction, bulk reaction, etc. In the case of solution reaction, the concentrations of the catalyst may be, by nickel conversion, in the range of from 0.0001 millimol to 100 mole, preferably 0.001 millimol to 1 mol, more preferably 0.01 millimol to 100 millimole per liter of solvent.

The oligomerization reaction is effected at a temperature of from minus 100° C. to plus 200° C., preferably minus 50° C. to plus 100° C., more preferably 0° C. to 50° C. and as a pressure, of from 10 kPa.G to 10 MPa.G, preferably 100 kPa.G to 5 MPa.G, more preferably 200 kPa.G to 3 MPa.G. Reaction time lengths are not normally restricted, but may be from 1 minute to 1 week with a batch mode reaction and from 1 second to 6 hours with a continuous mode reaction in which both feedstock and catalyst are fed continuously while the reaction product is continuously withdrawn.

It has been found that a solution polymerization mode of reaction is particularly useful with use of a solvent of the kind which is free from adversely affecting the inventive oligomerization catalyst and which may be such solvents that are used in the preparation of the inventive catalyst, or it may alternatively be a starting monomer for oligomerization.

The oligomerization reaction according to the invention is initiated by introducing the catalyst and a given α-olefin feedstock into a pressure vessel, the feedstock being normally (at 0° C. and 1 atmospheric) gaseous or liquid. Upon completion of the reaction, the vessel is depressurized and released in the air, followed by washing the reaction product with dilute chloric acid and then with saturated salt water and finally by drying the product with magnesium sulfate. Distillation is preferred for refining the product.

There may be produced various α-olefinic oligomers, but dimers in particular can be produced with a high rate of selectively according to the invention. For example, there may be produced 1-butene and 2-butene from ethylene, and 1-hexene, 2-hexene, 2-methyl-1-pentene, 2-methyl-2-pentene, 4-methyl-1-pentene, 4-methyl-2-pentene, 2,3-dimethyl-1-butene and 2,3-dimethyl-2-butene from propylene.

Industrial Utility of the Invention

The inventive catalyst is highly industrially useful as it is capable of selectively producing dimer products, particularly propylene oligomers of an unsaturated $C_6$ composition comprising chiefly 2,3-dimethyl-1-butene and 2,3-dimethyl-2-butene and containing hexenes and methylpentenes. The resulting product is useful as a gasoline blend or octane improver. The $C_6$ composition may be hydrogenated to provide a 2,3-dimethylbutane-rich product for use as a high-performance gasoline blend or octane improver.

The invention will be further described by way of the following examples which should be regarded only as illustrative, not in a limiting sense.

INVENTIVE EXAMPLE 1

A 500 ml autoclave equipped with an electromagnetic stirrer and fully dried was charged under nitrogen atmosphere with 130 ml dry toluene, a toluene solution (0.17 mmol) of nickel naphthenate, 1,5-cyclooctadiene (2.3 mmole) and triisopropylphosphine (0.17 mmol) while being stirred, followed by addition of a mixture of 1,3-bis-(trifluoromethyl)-benzene (0.17 mol) and a toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 80% |
|---|---|
| Catalytic activity | 18,000 converted C'$_3$ mol/Ni mol |
| Dimer selectivity | 94% |
| Dimethylbutene selectivity | 45% |
| Methylpentene selectivity | 50% |
| Hexene selectivity | 5% |

INVENTIVE EXAMPLE 2

A 500 ml autoclave equipped with an electromagnetic stirrer and fully dried was charged under nitrogen atmosphere with 130 ml dry toluene, bis-(acetonate)-nickel (0.17 mmol), triphenylphosphine (0.17 mmol), 2-methyl-1,3-butadiene (2.3 mmole), perfluorodecaline (0.17 mmol) and a toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total diners (100%).

| Propylene conversion | 89% |
|---|---|
| Catalytic activity | 17,000 converted C'$_3$ mol/Ni mol |
| Dimer selectivity | 94% |
| Dimethylbutene selectivity | 15% |
| Methylpentene selectivity | 40% |
| Hexene selectivity | 45% |

INVENTIVE EXAMPLE 3

The procedure of Inventive Example 1 was followed except that cyclooctadiene was not used.

| Propylene conversion | 77% |
|---|---|
| Catalytic activity | 9,000 converted C'$_3$ mol/Ni mol |
| Dimer selectivity | 93% |
| Dimethylbutene selectivity | 45% |
| Methylpentene selectivity | 47% |
| Hexene selectivity | 8% |

INVENTIVE EXAMPLE 4

A 500 ml autoclave equipped with an electromagnetic stirrer and fully dried was charged under nitrogen atmosphere with 130 ml dry toluene, nickel acetate (0.17 mmol) and tricyclohexylphosphine (0.6 mmol) while being stirred, followed by addition of a mixture of hexafluorobenzene (0.17 mmol), 1,3-butadiene (23 mmole) and ethyl-di(2,6-di-t-butyl-4-methylphenoxy)-aluminum (15 mmole). N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 55% |
|---|---|
| Catalytic activity | 6,000 converted C'$_3$ mol/Ni mol |
| Dimer selectivity | 98% |
| Dimethylbutene selectivity | 45% |
| Methylpentene selectivity | 47% |
| Hexene selectivity | 8% |

INVENTIVE EXAMPLE 5

The procedure of Inventive Example 1 was followed except that trifluoroethyltolytyl ether (0.2 mmol) was used in place of 1,3-bis-(trifluoromethyl)-benzene and that 1,5-cyclooctadiene was not used.

| Propylene conversion | 60% |
|---|---|
| Catalytic activity | 7,500 converted C'$_3$ mol/Ni mol |
| Dimer selectivity | 100% |
| Dimethylbutene selectivity | 45% |
| Methylpentene selectivity | 47% |
| Hexene selectivity | 8% |

INVENTIVE EXAMPLE 6

The procedure of Inventive Example 1 was followed except that bis-(1,5-cyclooctadiene)-nickel (0.17 mmol) was used in place of nickel naphthanate, that trifluoroethyltriphenyl silylether (0.2 mmol) was used in place of 1,3-bis-(trifluoromethyl)-benzene and that 1,5-cyclooctadiene was not used.

| Propylene conversion | 60% |
|---|---|
| Catalytic activity | 6,000 converted C'$_3$ mol/Ni mol |
| Dimer selectivity | 100% |
| Dimethylbutene selectivity | 40% |
| Methylpentene selectivity | 52% |
| Hexene selectivity | 8% |

INVENTIVE EXAMPLE 7

The procedure of Inventive Example 1 was followed except that 3-perfluorohexyl-1,2-epoxypropane (0.17 mmol) was used in place of 1,3-bis-(trifluoromethyl)-benzene and that 1,5-cyclooctadiene was not used.

| | |
|---|---|
| Propylene conversion | 45% |
| Catalytic activity | 4,000 converted C'$_3$ mol/Ni mol |
| Dimer selectivity | 100% |
| Dimethylbutene selectivity | 41% |
| Methylpentene selectivity | 52% |
| Hexene selectivity | 7% |

INVENTIVE EXAMPLE 8

The procedure of Inventive Example 1 was followed except that 2,2-bisethoxy-1,1,1,3,3,3-hexafluoropropane (0.17 mmol) was used in place of 1,3-bis-(trifluoromethyl)-benzene and that 1,5-cyclooctadiene was not used.

| | |
|---|---|
| Propylene conversion | 45% |
| Catalytic activity | 3,900 converted C'$_3$ mol/Ni mol |
| Dimer selectivity | 100% |
| Dimethylbutene selectivity | 41% |
| Methylpentene selectivity | 49% |
| Hexene selectivity | 10% |

INVENTIVE EXAMPLE 9

The procedure of Inventive Example 1 was followed except that 2,2-bis-(2,2,2-trifluoroethoxy)-propane (0.17 mmol) was used in place of 1,3-bis-(trifluoromethyl)-benzene and that 1,5-cyclooctadiene was not used.

| | |
|---|---|
| Propylene conversion | 30% |
| Catalytic activity | 2,900 converted C'$_3$ mol/Ni mol |
| Dimer selectivity | 100% |
| Dimethylbutene selectivity | 33% |
| Methylpentene selectivity | 52% |
| Hexene selectivity | 15% |

INVENTIVE EXAMPLE 10

The procedure of Inventive Example 1 was followed except that chloropentafluorobenzene (0.17 mmol) was used in place of 1,3-bis-(trifluoromethyl)-benzene and that 1,5-cyclooctadiene was not used.

| | |
|---|---|
| Propylene conversion | 69% |
| Catalytic activity | 7,500 converted C'$_3$ mol/Ni mol |
| Dimer selectivity | 97% |
| Dimethylbutene selectivity | 42% |
| Methylpentene selectivity | 52% |
| Hexene selectivity | 6% |

INVENTIVE EXAMPLE 11

The procedure of Inventive Example 1 was followed except that 1,1,1-triethoxy-2,2,2-trifluoroethane (0.17 mmol) was used in place of 1,3-biz-(trifluoromethyl)-benzene and that 1,5-cyclooctadiene was not used.

| | |
|---|---|
| Propylene conversion | 39% |
| Catalytic activity | 3,500 converted C'$_3$ mol/Ni mol |
| Dimer selectivity | 91% |
| Dimethylbutene selectivity | 39% |
| Methylpentene selectivity | 52% |
| Hexene selectivity | 9% |

INVENTIVE EXAMPLE 12

The procedure of Inventive Example 1 was followed except that 1,1,1-tri-(2,2,2-trifluoroethoxy)-ethane (0.17 mmol) was used in place of 1,3-bis-(trifluorometyl)-benzene and that 1,5-cyclooctadiene was not used.

| | |
|---|---|
| Propylene conversion | 30% |
| Catalytic activity | 3,000 converted C'$_3$ mol/Ni mol |
| Dimer selectivity | 91% |
| Dimethylbutene selectivity | 39% |
| Methylpentene selectivity | 52% |
| Hexene selectivity | 9% |

INVENTIVE EXAMPLE 13

The procedure of Inventive Example 1 was followed except that 2,2,2-trifluoroethoxy ethylene oxide (0.17 mmol) was used in pace of 1,3-bis-(trifluoromethyl)-benzene and that 1,5-cyclooctadiene was not used.

| | |
|---|---|
| Propylene conversion | 30% |
| Catalytic activity | 3,100 converted C'$_3$ mol/Ni mol |
| Dimer selectivity | 91% |
| Dimethylbutene selectivity | 37% |
| Methylpentene selectivity | 52% |
| Hexene selectivity | 11% |

INVENTIVE EXAMPLE 14

The procedure of Inventive Example 1 was followed except that 2-trifluoromethylfuran (0.17 mmol) was used in pace of 1,3-bis-(trifluoromethyl)-benzene and that 1,5-cyclooctadiene was not used.

| | |
|---|---|
| Propylene conversion | 56% |
| Catalytic activity | 4,700 converted C'$_3$ mol/Ni mol |
| Dimer selectivity | 91% |
| Dimethylbutene selectivity | 42% |
| Methylpentene selectivity | 44% |
| Hexene selectivity | 14% |

INVENTIVE EXAMPLE 15

The procedure of Inventive Example 1 was followed except that 2-(2',2',2'-trifluoroethyl)-tetrahydrofuran (0.17 mmol) was used in pace of 1,3-bis-(trifluoromethyl)-benzene and that 1,5-cyclooctadiene was not used.

| | |
|---|---|
| Propylene conversion | 60% |
| Catalytic activity | 5,700 converted C'$_3$ mol/Ni mol |
| Dimer selectivity | 91% |
| Dimethylbutene selectivity | 42% |

| Methylpentene selectivity | 52% |
|---|---|
| Hexene selectivity | 7% |

INVENTIVE EXAMPLE 16

The procedure of Inventive Example 1 was followed except that 2-(2',2',2'-trifluoroethyl)-tetrahydropyran (0.17 mmol) was used in pace of 1,3-bis-(trifluoromethyl)-benzene and that 1,5-cyclooctadiene was not used.

| Propylene conversion | 62% |
|---|---|
| Catalytic activity | 5,600 converted $C_3$ mol/Ni mol |
| Dimer selectivity | 94% |
| Dimethylbutene selectivity | 41% |
| Methylpentene selectivity | 52% |
| Hexene selectivity | 7% |

INVENTIVE EXAMPLE 17

The procedure of Inventive Example 1 was followed except that 2-(2',2',2'-trifluoroethoxy)-tetrahydropyran (0.17 mmol) was used in pace of 1,3-bis-(trifluoromethyl)-benzene and that 1,5-cyclooctadiene was not used.

| Propylene conversion | 42% |
|---|---|
| Catalytic activity | 3,600 converted $C_3$ mol/Ni mol |
| Dimer selectivity | 94% |
| Dimethylbutene selectivity | 37% |
| Methylpentene selectivity | 50% |
| Hexene selectivity | 13% |

INVENTIVE EXAMPLE 18

The procedure of Inventive Example 1 was followed except that 2-(2',2',2'-trifluoroethoxy)-tetrahydrofuran(0.17 mmol) was used in pace of 1,3-bis-(trifluoromethyl)-benzene and that 1,5-cyclooctadiene was not used.

| Propylene conversion | 45% |
|---|---|
| Catalytic activity | 3,700 converted $C_3$ mol/Ni mol |
| Dimer selectivity | 94% |
| Dimethylbutene selectivity | 37% |
| Methylpentene selectivity | 53% |
| Hexene selectivity | 10% |

INVENTIVE EXAMPLE 19

A 500 ml autoclave equipped with an electromagnetic stirrer and fully dried was charged under nitrogen atmosphere with 130 ml dry toluene, bis-(1,5-cyclooctadiene)-nickel (0.17 mmol) and triisopropylphosphine (0.17 mmol) while being stirred, followed by addition of a mixture of 1,3-bis-(trifluoromethyl)-benzene (0.17 mmol) and a toluene solution (1.1 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 77% |
|---|---|
| Catalytic activity | 17,500 converted $C_3$ mol/Ni mol |
| Dimer selectivity | 98% |
| Dimethylbutene selectivity | 47% |
| Methylpentene selectivity | 47% |
| Hexene selectivity | 6% |

INVENTIVE EXAMPLE 20

The procedure of Inventive Example 19 was followed except that triphenylphosphine (0.40 mmol) was used in place of triisopropylphosphine.

| Propylene conversion | 87% |
|---|---|
| Catalytic activity | 18,500 converted $C_3$ mol/Ni mol |
| Dimer selectivity | 90% |
| Dimethylbutene selectivity | 8% |
| Methylpentene selectivity | 36% |
| Hexene selectivity | 56% |

INVENTIVE EXAMPLE 21

A 500 ml autoclave equipped with an electromagnetic stirrer and fully dried was charged under nitrogen atmosphere with 130 ml dry toluene, a toluene solution (0.17 mmol) of nickel 2-ethylhexanate, vinylnorbornene (0.9 mmol) and tricyclohexylphosphine (0.17 mmol) while being stirred, followed by addition of a mixture of 1,3-bis-(trifluoromethyl)-benzene (0.17 mmol) and a toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 80% |
|---|---|
| Catalytic activity | 21,000 converted $C_3$ mol/Ni mol |
| Dimer selectivity | 94% |
| Dimethylbutene selectivity | 47% |
| Methylpentene selectivity | 48% |
| Hexene selectivity | 5% |

COMPARATIVE EXAMPLE 1

The procedure of Inventive Example 1 was followed except that both 1,3-bis-(trifluoromethyl)-benzene and 1,5-cyclooctadiene were not used.

| | |
|---|---|
| Propylene conversion | 15% |
| Catalytic activity | 500 converted $C_3$ mol/Ni mol |
| Dimer selectivity | 94% |
| Dimethylbutene selectivity | 37% |
| Methylpentene selectivity | 57% |
| Hexene selectivity | 6% |

INVENTIVE EXAMPLE 22

A 500 ml autoclave equipped with an electromagnetic stirrer and fully dried was charged under nitrogen atmosphere with 130 ml dry toluene, bis-(1,5-cyclooctadiene)-nickel (0.17 mmol) and triisopropylphosphine (0.17 mmol) while being stirred, followed by addition of a mixture of tungsten phosphate (0.17 mmol) and a toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 71% |
| Catalytic activity | 15,000 converted $C_3$ mol/Ni mol |
| Dimer selectivity | 94% |
| Dimethylbutene selectivity | 43% |
| Methylpentene selectivity | 50% |
| Hexene selectivity | 7% |

INVENTIVE EXAMPLE 23

A 500 ml autoclave equipped with an electromagnetic stirrer and fully dried was charged under nitrogen atmosphere with 130 ml dry toluene, nickel acetate (0.17 mmol), triphenylphosphine (0.17 mmol), 2-methyl-1,3-butadiene (2.3 mmol) and tungsten silicate (0.17 mmol) while being stirred, followed by addition of a toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 65% |
| Catalytic activity | 13,500 converted $C_3$ mol/Ni mol |
| Dimer selectivity | 94% |
| Dimethylbutene selectivity | 11% |
| Methylpentene selectivity | 40% |
| Hexene selectivity | 49% |

INVENTIVE EXAMPLE 24

A 500 ml autoclave equipped with an electromagnetic stirrer and fully dried was charged under nitrogen atmosphere with 130 ml dry toluene, a toluene solution (0.17 mmol) of nickel naphthenate, 1,5-cyclooctadiene (23 mmole) and triisopropylphosphine (0.17 mmol) while being stirred, followed by addition of a mixture of molybdenum phosphate (0.17 mmol) and a toluene solution (1.1 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 67% |
| Catalytic activity | 13,000 converted $C_3$ mol/Ni mol |
| Dimer selectivity | 97% |
| Dimethylbutene selectivity | 45% |
| Methylpentene selectivity | 49% |
| Hexene selectivity | 6% |

INVENTIVE EXAMPLE 25

A 500 ml autoclave equipped with an electromagnetic stirrer and fully dried was charged under nitrogen atmosphere with 130 ml dry toluene, a toluene solution (0.17 mmol) of nickel naphthenate and tricyclohexylphosphine (0.6 mmol) while being stirred, followed by addition of a mixture of 1,3-butadiene (23 mmole), molybdic acid (0.17 mmol) and 2,6-di-t-butyl-4-methylphenoxy aluminum (15 mmole). N-decane (10 ml) was also added as an internal reference compound.

The admixture was continuously stirred at 40° C., to which propylene feedstock was added under a feed pressure maintained at 4 kgf/cm².G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 49% |
| Catalytic activity | 3,500 converted $C_3$ mol/Ni mol |
| Dimer selectivity | 98% |

| Dimethylbutene selectivity | 43% |
|---|---|
| Methylpentene selectivity | 49% |
| Hexene selectivity | 8% |

INVENTIVE EXAMPLE 26

A 500 ml autoclave equipped with an electromagnetic stirrer and fully dried was charged under nitrogen atmosphere with 130 ml dry toluene, nickel acetate (0.17 mmol), 1,5-cyclooctadiene (23 mmole) and triisopropylphosphine (0.17 mmol) while being stirred, followed by addition of a mixture of molybdenum silicate (0.17 mmol) and a toluene solution (1.1 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm$^2$.G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 66% |
|---|---|
| Catalytic activity | 12,800 converted C'$_3$ mol/Ni mol |
| Dimer selectivity | 97% |
| Dimethylbutene selectivity | 42% |
| Methylpentene selectivity | 49% |
| Hexene selectivity | 9% |

INVENTIVE EXAMPLE 27

A 500 ml autoclave equipped with an electromagnetic stirrer and fully dried was charged under nitrogen atmosphere with 130 ml dry toluene, nickel acetate (0.17 mmol), 2-methyl-1,3-butadiene (23 mmole) and tricyclohexylphosphine (0.17 mmol) while being stirred, followed by addition of a mixture of tungstic acid (0.17 mmol) and a toluene solution (1.1 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm$^2$.G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 65% |
|---|---|
| Catalytic activity | 11,100 converted C'$_3$ mol/Ni mol |
| Dimer selectivity | 97% |
| Dimethylbutene selectivity | 40% |
| Methylpentene selectivity | 51% |
| Hexene selectivity | 9% |

INVENTIVE EXAMPLE 28

The procedure of Inventive Example 24 was followed except that 1,5-cyclooctadiene was not used.

| Propylene conversion | 57% |
|---|---|
| Catalytic activity | 9,000 converted C'$_3$ mol/Ni mol |
| Dimer selectivity | 93% |
| Dimethylbutene selectivity | 40% |
| Methylpentene selectivity | 51% |
| Hexene selectivity | 9% |

INVENTIVE EXAMPLE 29

A 500 ml autoclave equipped with an electromagnetic stirrer and fully dried was charged under nitrogen atmosphere with 130 ml dry toluene, nickel 2-ethylhexanate (0.17 mmol), tricyclohexylphospine (0.17 mmol), vinylnorbornen (1.0 mmol) and tungsten silicate (0.17 mmol) while being stirred, followed by addition of toluene solution (2.3 mmole) of ethylaluminum sesquichloride. N-decane (10 ml) was also added as an internal reference compound.

The admixture was continuously stirred at 40° C., to which propylene feedstock was added under a feed pressure maintained at 4 kgf/cm$^2$.G, and the reaction was continued for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 65% |
|---|---|
| Catalytic activity | 13,500 converted C'$_3$ mol/Ni mol |
| Dimer selectivity | 94% |
| Dimethylbutene selectivity | 48% |
| Methylpentene selectivity | 45% |
| Hexene selectivity | 7% |

INVENTIVE EXAMPLE 30

A 500 ml autoclave equipped with an electromagnetic stirrer and fully dried was charged under nitrogen atmosphere with 40 ml dry toluene, a toluene solution (0.1 mmol) of nickel naphthenate and triisopropylphosphine (0.1 mmol) while being stirred, followed by addition of a mixture of sodium para-tolenesulfonate (0.1 mmol) and a toluene solution (2.3 mmole) of ethylaluminum sesquichloride. N-decane (10 ml) was also added as an internal reference compound.

The admixture was continuously stirred at 40° C., to which propylene feedstock was added with the system pressure maintained at 686 kPa.G, and the reaction was continued for 1 hour. Upon completion of the reaction, propylene was expelled and the reaction solution was washed with dilute chloric acid and saturated salt water, followed by drying with anhydrous magnesium sulfate. The reaction product (oligomer) was gas-chromatographically analyzed with the results shown below wherein selectivity of dimethylbutene, methylpentene and hexene, respectively, is given by percentage on the basis of total dimers (100%).

| | |
|---|---|
| Propylene conversion | 84% |
| Catalytic activity | 21,000 converted $C'_3$ mol/Ni mol |
| Dimer selectivity | 94% |
| Dimethylbutene selectivity | 49% |
| Methylpentene selectivity | 44% |
| Hexene selectivity | 7% |

INVENTIVE EXAMPLE 31

A 500 ml autoclave equipped with an electromagnetic stirrer and fully dried was charged under nitrogen atmosphere with 40 ml dry toluene, bis-(1,5-cyclooctadiene)-nickel (0.1 mmol), triphenylphosphine (1.5 mmole), 2-methyl-1,3-butadiene (2.3 mmole) and potassium methanesulfonate (0.1 mmol) while being stirred, followed by addition of a toluene solution (2.3 mmole) of ethylaluminum sesquichloride. N-decane (10 ml) was also added as an internal reference compound.

The admixture was continuously stirred at 40° C., to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 88% |
| Catalytic activity | 25,000 converted $C'_3$ mol/Ni mol |
| Dimer selectivity | 94% |
| Dimethylbutene selectivity | 6% |
| Methylpentene selectivity | 54% |
| Hexene selectivity | 40% |

INVENTIVE EXAMPLE 32

A 500 ml autoclave equipped with an electromagnetic stirrer and fully dried was charged under nitrogen atmosphere with 40 ml dry toluene, a toluene solution (0.1 mmol) of nickel naphthenate, 1,5-cyclooctadiene (23 mmole) and tricyclohexylphosphine (0.1 mmol) while being stirred, followed by addition of trifluoromethanesulfonate (0.1 mmol) and a toluene solution (1.1 mmole) of ethylaluminum sesquichloride. N-decane (10 ml) was also added as an internal reference compound.

The admixture was continuously stirred at 40° C., to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 89% |
| Catalytic activity | 27,000 converted $C'_3$ mol/Ni mol |
| Dimer selectivity | 97% |
| Dimethylbutene selectivity | 40% |
| Methylpentene selectivity | 49% |
| Hexene selectivity | 11% |

INVENTIVE EXAMPLE 33

A 500 ml autoclave equipped with an electromagnetic stirrer and fully dried was charged under nitrogen atmosphere with 40 ml dry toluene, acetylacetonate nickel (0.1 mmol) and tricyclohexylphosphine (0.6 mmol) while being stirred, followed by addition of a mixture at −78° C. of 1,3-butadiene (23 mmole), methylbenzene sulfonate (0.1 mmol) and 2,6-di-t-butyl-4-methylphenoxy aluminum (15 mmole). N-decane (10 ml) was also added as an internal reference compound.

The admixture was continuously stirred at 40° C., to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 41% |
| Catalytic activity | 3,900 converted $C'_3$ mol/Ni mol |
| Dimer selectivity | 98% |
| Dimethylbutene selectivity | 42% |
| Methylpentene selectivity | 50% |
| Hexene selectivity | 8% |

INVENTIVE EXAMPLE 34

A 500 ml autoclave equipped with an electromagnetic stirrer and fully dried was charged under nitrogen atmosphere with 40 ml dry toluene, nickel acetate (0.1 mmol), 1,5-cyclooctadiene (23 mmole) and triisopropylphosphine (0.1 mmol) while being stirred, followed by addition of a mixture of paratoluene sulfonate (0.1 mmol) and a toluene solution (1.1 mmole) of diethylaluminum chloride. N-decane (10 ml) was also added as an internal reference compound.

The admixture was continuously stirred at 40° C., to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 85% |
|---|---|
| Catalytic activity | 11,000 converted C'₃ mol/Ni mol |
| Dimer selectivity | 97% |
| Dimethylbutene selectivity | 41% |
| Methylpentene selectivity | 49% |
| Hexene selectivity | 10% |

INVENTIVE EXAMPLE 35

A 500 ml autoclave equipped with an electromagnetic stirrer and fully dried was charged under nitrogen atmosphere with 40 ml dry toluene, a toluene solution of nickel 2-ethylhexanate (0.1 mmol), ethylidenenorbornene (23 mmole) and triisopropylphosphine (0.1 mmol) while being stirred, followed by addition of a mixture of a dichloromethane solution (0.5M, 0.2 ml and 0.1 mmol) of trifluoromethane sulfonate and a toluene solution (1.1 mmol) of ethylaluminum sesquichloride. N-decane (10 ml) was also added as an internal reference compound.

The admixture was continuously stirred at 40° C., to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 83% |
|---|---|
| Catalytic activity | 24,000 converted C'₃ mol/Ni mol |
| Dimer selectivity | 97% |
| Dimethylbutene selectivity | 40% |
| Methylpentene selectivity | 50% |
| Hexene selectivity | 10% |

INVENTIVE EXAMPLE 36

The procedure of Inventive Example 32 was followed except that 1,5-cyclooctadiene was not used.

| Propylene conversion | 61% |
|---|---|
| Catalytic activity | 12,000 converted C'₃ mol/Ni mol |
| Dimer selectivity | 93% |
| Dimethylbutene selectivity | 39% |
| Methylpentene selectivity | 50% |
| Hexene selectivity | 11% |

INVENTIVE EXAMPLE 37

A 500 ml autoclave equipped with an electromagnetic stirrer and fully dried was charged under nitrogen atmosphere with 100 ml dry ethanol, nickel chloride hexahydrate (0.1 mmol) and triphenylphosphine (0.2 mmol) while being stirred. After stirring at 40° C. for 1 hour, the supernatant ethanol solution was removed by syringe. The autoclave was well dried in vacuum, followed by addition of 50 ml toluene. Then, trifluoromethane sulfonate (0.04 mmol) and a toluene solution (2.1 mmole) of ethylaluminum sesquichloride were added. N-decane (10 ml) was also added as an internal reference compound.

The admixture was stirred at 40° C. for 5 minutes, to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 70% |
|---|---|
| Catalytic activity | 17,000 converted C'₃ mol/Ni mol |
| Dimer selectivity | 97% |
| Dimethylbutene selectivity | 11% |
| Methylpentene selectivity | 58% |
| Hexene selectivity | 31% |

INVENTIVE EXAMPLE 38

A 500 ml autoclave equipped with an electromagnetic stirrer and fully dried was charged under nitrogen atmosphere with 40 ml dry toluene, a toluene solution (0.1 mmol) of nickel naphthenate, vinylnorbornene (0.7 mmol) and tricyclohexylphosphine (0.1 mmol) while being stirred, followed by addition of a mixture of sodium trifluoromethane sulfonate (0.1 mmol) and a toluene solution (2.3 mmole) of ethylaluminum sesquichloride together with n-decane (10 ml) as an internal reference compound.

The admixture was stirred at 40° C. for 5 minutes, to which propylene feedstock was added with the system pressure maintained at 686 kPa.G, and the reaction was continued for for 1 hour. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 84% |
|---|---|
| Catalytic activity | 22,000 converted C'₃ mol/Ni mol |
| Dimer selectivity | 94% |
| Dimethylbutene selectivity | 48% |
| Methylpentene selectivity | 46% |
| Hexene selectivity | 6% |

COMPARATIVE EXAMPLE 2

The procedure of Inventive Example 32 was followed except that trifluoromethane sulfonate and 1,5-cyclooctadiene were not used.

| Propylene conversion | 10% |
|---|---|
| Catalytic activity | 700 converted C'₃ mol/Ni mol |
| Dimer selectivity | 94% |
| Dimethylbutene selectivity | 37% |
| Methylpentene selectivity | 57% |
| Hexene selectivity | 6% |

INVENTIVE EXAMPLE 39

A 500 ml autoclave equipped with an electromagnetic stirrer and fully dried was charged under nitrogen atmosphere with 40 ml dry toluene, nickel acetate (0.1 mmol), ethylidene norbornene (23 mmole) and triisopropylphosphine (0.1 mmol) while being stirred, followed by addition of a toluene solution (1.1 mmole) of ethylaluminum sesquichloride, n-decane (10 ml) as an internal reference compound and titanium chloride (IV)(0.01 mmol).

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 83% |
|---|---|
| Catalytic activity | 20,000 converted $C'_3$ mol/Ni mol |
| Dimer selectivity | 97% |
| Dimethylbutene selectivity | 41% |
| Methylpentene selectivity | 51% |
| Hexene selectivity | 8% |

INVENTIVE EXAMPLE 40

A 500 ml autoclave equipped with an electromagnetic stirrer and fully dried was charged under nitrogen atmosphere with 40 ml dry toluene, bis-(1,5-cyclooctadiene)-nickel (0.1 mmol) and triisopropylphosphine (0.1 mmol) while being stirred, followed by addition of a mixture of magnesium chloride (0.1 mmol) and a toluene solution (2.3 mmole) of diethylaluminum chloride. N-decane (10 ml) was then added as an internal reference compound.

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 79% |
|---|---|
| Catalytic activity | 11,000 converted $C'_3$ mol/Ni mol |
| Dimer selectivity | 94% |
| Dimethylbutene selectivity | 41% |
| Methylpentene selectivity | 50% |
| Hexene selectivity | 9% |

INVENTIVE EXAMPLE 41

A 500 ml autoclave equipped with an electromagnetic stirrer and fully dried was charged under nitrogen atmosphere with 40 ml dry toluene, a toluene solution (0.1 mmol) of nickel naphthenate, 1,5-cyclooctadiene (23 mmole) and tricyclohexylphosphine (0.1 mmol) while being stirred, followed by addition of a toluene solution (1.1 mmole) of ethylaluminum sesquichloride and n-decane (10 ml) as an internal reference compound. A toluene solution of tetrabutoxy zirconium (0.1 mmol) was then added.

The admixture was stirred at 400° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 88% |
|---|---|
| Catalytic activity | 25,000 converted $C'_3$ mol/Ni mol |
| Dimer selectivity | 97% |
| Dimethylbutene selectivity | 49% |
| Methylpentene selectivity | 45% |
| Hexene selectivity | 6% |

INVENTIVE EXAMPLE 42

The procedure of Inventive Example 41 was followed except that 1,5-cyclooctadiene was not used.

| Propylene conversion | 59% |
|---|---|
| Catalytic activity | 11,000 converted $C'_3$ mol/Ni mol |
| Dimer selectivity | 93% |
| Dimethylbutene selectivity | 41% |
| Methylpentene selectivity | 50% |
| Hexene selectivity | 9% |

INVENTIVE EXAMPLE 43

A 500 ml autoclave equipped with an electromagnetic stirrer and fully dried was charged under nitrogen atmosphere, with 40 ml dry toluene, a toluene solution (0.1 mmol) of nickel naphthenate, and tricyclohexylphosphine (0.6 mmol) while being stirred, followed by addition of a mixture at −78° C. of 1,3-butadiene (23 mmole) and 2,6-di-t-butyl-4-methylphenoxy aluminum (15 mmole). N-decane (10 ml) was added as an internal reference compound. Dibutyltinchloride (0.05 mmol) was also added.

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 40% |
|---|---|
| Catalytic activity | 4,000 converted $C'_3$ mol/Ni mol |
| Dimer selectivity | 98% |
| Dimethylbutene selectivity | 42% |
| Methylpentene selectivity | 49% |
| Hexene selectivity | 9% |

INVENTIVE EXAMPLE 44

A 500 ml autoclave equipped with an electromagnetic stirrer and fully dried was charged under nitrogen atmosphere with 40 ml dry toluene, a toluene solution (0.1 mmol) of nickel naphthenate, ethylidennorbornene (23 mmole) and triisopropylphosphine (0.1 mmol) while being stirred, followed by addition of a toluene solution (1.1 mmole) of ethylaluminum sesquichloride, n-decane (10 ml) as an internal reference compound and tetraisopropoxy titanium (0.1 mmol).

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 85% |
|---|---|
| Catalytic activity | 23,500 converted C'$_3$ mol/Ni mol |
| Dimer selectivity | 97% |
| Dimethylbutene selectivity | 47% |
| Methylpentene selectivity | 45% |
| Hexene selectivity | 8% |

INVENTIVE EXAMPLE 45

A 500 ml autoclave equipped with an electromagnetic stirrer and fully dried was charged under nitrogen atmosphere with 40 ml dry toluene, a toluene solution (0.1 mmol) of nickel 2-ethylhexanate, triphenylphosphine (1 mmol), 2-methyl-1,3-butadiene (2.3 mmole) and triphenyltin chloride (0.01 mmol), followed by addition of a toluene solution (2.3 mmole) of ethylaluminum sesquichloride and n-decane (10 ml) as an internal reference compound.

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 83% |
|---|---|
| Catalytic activity | 23,000 converted C'$_3$ mol/Ni mol |
| Dimer selectivity | 94% |
| Dimethylbutene selectivity | 7% |
| Methylpentene selectivity | 44% |
| Hexene selectivity | 49% |

INVENTIVE EXAMPLE 46

A 500 ml autoclave equipped with an electromagnetic stirrer and fully dried was charged under nitrogen atmosphere with 40 ml dry toluene, bis-(acetylacetonate)-nickel (0.1 mmol), 1,5-cyclooctadiene (23 mmole) and triisopropylphosphine (0.1 mmol) while being stirred, followed by addition of a toluene solution (1.1 mmole) of ethylaluminum sesquichloride, n-decane (10 ml) as an internal reference compound and a toluene solution of boron fluoride (III) diethyl ether complex (0.1 mmol).

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 82% |
|---|---|
| Catalytic activity | 24,000 converted C'$_3$ mol/Ni mol |
| Dimer selectivity | 97% |
| Dimethylbutene selectivity | 49% |
| Methylpentene selectivity | 44% |
| Hexene selectivity | 7% |

INVENTIVE EXAMPLE 47

A 500 ml autoclave equipped with an electromagnetic stirrer and fully dried was charged under nitrogen atmosphere with 40 ml dry toluene, a toluene solution (0.1 mmol) of nickel naphthenate, ethylidennorbonene (23 mmole) and tricyclohexylphosphine (0.1 mmol) while being stirred, followed by addition of a toluene solution (1.1 mmole) of ethylaluminum sesquichloride and n-decane (10 ml) as an internal reference compound. Tributyltin hydride (0.1 mmol) was also added.

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| Propylene conversion | 70% |
|---|---|
| Catalytic activity | 16,000 converted C'$_3$ mol/Ni mol |
| Dimer selectivity | 97% |
| Dimethylbutene selectivity | 49% |
| Methylpentene selectivity | 42% |
| Hexene selectivity | 9% |

INVENTIVE EXAMPLE 48

A 500 ml autoclave equipped with an electromagnetic stirrer and fully dried was charged under nitrogen atmosphere with 40 ml dry toluene, a toluene solution (0.1 mmol) of nickel naphthenate, 2-methfylbutadiene (23 mmole) and triisopropylphosphine (0.1 mmol) while being stirred, followed by addition of a toluene solution (1.1 mmole) of ethylaluminum sesquichloride, n-decane (10 ml) as an internal reference compound and diethylzinc (0.1 mmol).

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 77% |
| Catalytic activity | 20,000 converted $C'_3$ mol/Ni mol |
| Dimer selectivity | 97% |
| Dimethylbutene selectivity | 40% |
| Methylpentene selectivity | 52% |
| Hexene selectivity | 8% |

INVENTIVE EXAMPLE 49

The procedure of Inventive Example 41 was followed except that a butanol solution of (Zr:Butanol=1:1 mol) tetrabutoxy zirconium (0.1 mmol) was used in place of a toluene solution of tetrabutoxy zirconium (0.1 mmol).

| | |
|---|---|
| Propylene conversion | 88% |
| Catalytic activity | 25,000 converted $C'_3$ mol/Ni mol |
| Dimer selectivity | 97% |
| Dimethylbutene selectivity | 49% |
| Methylpentene selectivity | 45% |
| Hexene selectivity | 6% |

INVENTIVE EXAMPLE 50

A 500 ml autoclave equipped with an electromagnetic stirrer and fully dried was charged under nitrogen atmosphere with 40 ml dry toluene, nickel 2-ethylhexanate (0.1 mmol), vinylnorbornene (0.5 mmol) and triisopropylphosphine (0.1 mmol) while being stirred, followed by addition of a toluene solution (1.1 mmole) of ethylaluminum sesquichloride, n-decane (10 ml) as an internal reference compound and sodium tetraphenylborate (0.01 mmol).

The admixture was stirred at 40° C. for 5 minutes, to which propylene feedstock was added. The reaction was continued for 1 hour with the system pressure maintained at 686 kPa.G. Upon completion of the reaction, propylene was expelled and the reaction solution was washed with dilute chloric acid and saturated salt water, followed by drying with anhydrous magnesium sulfate. The reaction product was gas-chromatographically analyzed with the results shown below wherein selectivity of dimethylbutene, methylpentene and hexene, respectively, is given by percentage on the basis of total dimers (100%).

| | |
|---|---|
| Propylene conversion | 83% |
| Catalytic activity | 22,000 converted $C'_3$ mol/Ni mol |
| Dimer selectivity | 97% |
| Dimethylbutene selectivity | 49% |
| Methylpentene selectivity | 44% |
| Hexene selectivity | 7% |

We claim:

1. An oligomerization catalyst for olefins which comprises a reaction product resulting from contacting the following components (A), (B), (C) and (D):

component (A) which is at least one nickel compound of the group consisting of a nickel salt of an organic acid, a nickel salt of an inorganic acid, and a nickel complex;

component (B) which is at least one organophosphoric compound of the formula

$$PX^1X^2X^3 \qquad (I)$$

wherein $X^1$, $X^2$ and $X^3$ each are a halogen atom, a hydrogen atom or a $C_1$–$C_{12}$ hydrocarbon residual group;

component (C) which is at least one organoalumium compound; and component (D) which is at least one compound selected from the group consisting of (a) at least one carbon-halogen bond-containing compound of any of the formulae

(X)

(XI)

(XII)

(XIII)

(XIV)

(XV)

(XVI)

$R^4-O-R^8$ (XVII)

$R^4-O-SiR^8{}_3$ (XVIII)

$R^4R^9C(OR^8)_2$ (XIX)

$R^4R^9C(OR^4)(OR^8)$ (XX)

$R^4C(OR^8)_3$ (XXI)

$R^8C(OR^4)(OR^8)_2$ (XXII)

$R^4-R^{10}$ (XXIII)

wherein $R^4$ is a $C_1$–$C_{30}$ halogenated hydrocarbon group, $R^8$ is $R^4$ or a $C_1$–$C_{30}$ hydrocarbon group, $R^9$ is the same as $R^8$ or a hydrogen atom and $R^{10}$ is a hydrogen or halogen atom;

(b) oxoacid and salts thereof; and (c) compounds of any of the formulae $QX^4{}_n$ (II)

$QR_n$ (III)

$QR'_n$ (IV)

$QX^4{}_l R_m$ (V)

$QX^4{}_l R'_m$ (VI)

$QR_l R'_m$ (VII)

$$Q^1(BR_4)_p \qquad (VIII)$$

and $$R''(BR_4) \qquad (IX)$$

wherein Q is an element of the group consisting of Mg, Ti, Zr, B, and Sn; $Q^1$ is an element of the group consisting of Li, Na, K, Ca, and Zn; $X^4$ is a halogen or hydrogen atom; R is a $C_1$–$C_{12}$ hydrocarbon group; R' is a $C_1$–$C_{12}$ oxygen-containing hydrocarbon group; R'' is a $C_1$–$C_{20}$ hydrocarbon group or an ammonium group; n is a valence of Q; l and m are natural numbers that satisfy n=l+m; and p is a valence of $Q^1$.

2. An oligomerization catalyst according to claim 1 wherein said halogenated hydrocarbon group is a $C_1$–$C_{30}$ hydrocarbon group having hydrogen partially or wholly substituted with halogen.

3. An oligomerization catalyst according to claim 1 wherein said hydrocarbon group is selected from the group consisting of alkyl, alkenyl, aryl, and aralkyl groups.

4. An oligomerization catalyst according to claim 1 wherein said halogen is fluorine or chlorine.

5. An oligomerization catalyst according to claim 1 wherein said component (D) is a heteropolyacid or a salt thereof.

6. An oligomerization catalyst according to claim 5 wherein said heteropolyacid or salt thereof has a ligand of the group consisting of tungsten, molybdenum, and vanadium.

7. An oligomerization catalyst according to claim 1 wherein said nickel salt of an organic acid is carboxylate.

8. An oligomerization catalyst according to claim 1 wherein said hydrocarbon residual group in said component (B) is a hydrocarbon group of the group consisting of alkyl, aryl and aralkyl groups.

9. An oligomerization catalyst according to claim 1 wherein said organoaluminum compound in said component (C) is a compound of the formula $$AlR^1_p X_{3-p} \qquad (XXIV)$$

wherein $R^1$ is a $C_1$–$C_{20}$ hydrocarbon group, X is a hydrogen or halogen atom, and p is an integer that satisfies the range of $0 \leq n \leq 3$.

10. An oligomerization catalyst according to claim 9 wherein said hydrocarbon group is selected from the group consisting of alkyl, aryl, and aralkyl groups.

11. An oligomerization catalyst according to claim 1 wherein said component (B), said component (C) and said component (D) are added in amounts of 0.01–100 mole, 0.01–10,000 mole and 0.001–100 mole, respectively, per mol of said component (A).

12. An oligomerization catalyst according to claim 1 wherein said component (B), said component (C) and said component (D) are added in amounts of 0.1–10 mole, 0.1–1,000 mole and 0.01–10 mole, respectively, per mol of said component (A).

13. An oligomerization catalyst which contains a product of reaction between each of the components (A) through (D) defined in claim 1 and a $C_4$–$C_{20}$ nonaromatic hydrocarbon compound having two or more carbon-carbon double bonds.

14. An oligomerization catalyst according to claim 13 wherein said nonaromatic hydrocarbon compound is a compound selected from the group consisting of alkadienes, cycloalkadienes, and terpene unsaturated compounds.

15. A process of producing olefinic oligomers by reacting alpha-olefins in the presence of a catalyst containing a product of reaction between each of the components (A) through (D) defined in claim 1.

16. A process of producing olefinic oligomers by reacting alpha-olefins in the presence of the catalyst defined in claim 13.

17. A process of producing olefinic oligomers according to claim 15 wherein said alpha-olefin is propylene.

18. A process of producing olefinic oligomers according to claim 16 wherein said alpha-olefin is propylene.

* * * * *